US009499813B2

(12) United States Patent
Derda et al.

(10) Patent No.: US 9,499,813 B2
(45) Date of Patent: Nov. 22, 2016

(54) SYSTEMS AND METHODS FOR AMPLIFICATION AND PHAGE DISPLAY

(75) Inventors: Ratmir Derda, Cambridge, MA (US); Sindy K. Y. Tang, Stanford, CA (US); George M. Whitesides, Newton, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 400 days.

(21) Appl. No.: 13/702,603

(22) PCT Filed: Jun. 10, 2011

(86) PCT No.: PCT/US2011/039932
§ 371 (c)(1),
(2), (4) Date: Mar. 18, 2013

(87) PCT Pub. No.: WO2012/047324
PCT Pub. Date: Apr. 12, 2012

(65) Prior Publication Data
US 2013/0210680 A1    Aug. 15, 2013

Related U.S. Application Data

(60) Provisional application No. 61/353,324, filed on Jun. 10, 2010.

(51) Int. Cl.
*C12N 15/10* (2006.01)
*C40B 40/02* (2006.01)
*C40B 50/06* (2006.01)

(52) U.S. Cl.
CPC ........... *C12N 15/1037* (2013.01); *C40B 40/02* (2013.01); *C40B 50/06* (2013.01)

(58) Field of Classification Search
CPC .... C12N 15/1037; C40B 40/02; C40B 50/06
USPC .......................................................... 506/7
See application file for complete search history.

(56) References Cited

U.S. PATENT DOCUMENTS 4,416,796 A    11/1983   Bohm et al.
5,512,131 A    4/1996    Kumar et al.
(Continued)

FOREIGN PATENT DOCUMENTS

WO    9629629 A2     9/1996
WO    0013762 A1     3/2000
(Continued)

OTHER PUBLICATIONS

Rodi et al. (J. Mol. Biol., 2002, 322, 1039-1052).*
(Continued)

*Primary Examiner* — Larry Riggs
*Assistant Examiner* — Karla Dines
(74) *Attorney, Agent, or Firm* — Nixon Peabody LLP

(57) ABSTRACT

Embodiments of various aspects described herein are directed to amplification of biological entities, for example, for phage display. In one aspect, members of a library of biological entities are encapsulated in separate compartments (e.g., in separate microfluidic droplets) and amplified. For example, by putting members of a phage display library into microfluidic droplets such that no droplet contains more than one member of the library, the library can be amplified without any substantial changes in population distributions, or other artifacts created due to differences in growth rates or amplification between different members of the library. In some cases, the volume of the compartments can be used to control the copy number of a biological entity during amplification. This can be advantageous, for example, in preserving diversity within a library by preventing rapidly amplifying biological entities from outcompeting slowly amplifying biological entities.

18 Claims, 10 Drawing Sheets

(56) References Cited

U.S. PATENT DOCUMENTS

| | | | |
|---|---|---|---|
| 6,355,198 | B1 | 3/2002 | Kim et al. |
| 7,708,949 | B2 | 5/2010 | Stone et al. |
| 7,759,111 | B2 | 7/2010 | Lee et al. |
| 2003/0073811 | A1* | 4/2003 | Kozlowski ......... G01N 33/6845 530/350 |
| 2005/0003380 | A1 | 1/2005 | Cohen et al. |
| 2005/0123563 | A1* | 6/2005 | Doranz et al. ............. 424/204.1 |
| 2005/0172476 | A1 | 8/2005 | Stone et al. |
| 2006/0163385 | A1 | 7/2006 | Link et al. |
| 2007/0003442 | A1 | 1/2007 | Link et al. |
| 2010/0022414 | A1* | 1/2010 | Link et al. ...................... 506/18 |

FOREIGN PATENT DOCUMENTS

| | | |
|---|---|---|
| WO | 0189787 A2 | 11/2001 |
| WO | 2004002627 A2 | 1/2004 |
| WO | 2004091763 A2 | 10/2004 |
| WO | 2005021151 A1 | 3/2005 |
| WO | 2005/030957 | 4/2005 |
| WO | 2007149537 A2 | 12/2007 |
| WO | 2008021123 A1 | 2/2008 |
| WO | 2009/011808 | 1/2009 |
| WO | 2009005680 A1 | 1/2009 |
| WO | 2009148979 A2 | 12/2009 |

OTHER PUBLICATIONS

Jacobsson et al. (Biol. Proced. Online, 2003, 5(1), pp. 123-135).*
Morohashi et al.(Combinatorial Chemistry and High Throughput Screening, 2006, 9, pp. 51-61).*
Bertschinger et al., Protein Engineering, 17(9):699-707 (2004). "Covalent DNA display as a novel tool for directed evolution of protein in vitro."
Brammer et al., Analytical Biochemistry, 373(1):88-98 (2007). "A target-unrelated peptide in an M13 phage display library traced to an advantageous mutation in the gene II ribosome-binding site."
Clausell-Tormos et al., Chemistry and Biology, 15(5):427-437 (2008). "Droplet-based microfluidic platforms for the encapsulation and screening of mammalian cells and multicellular organisms."
Derda et al., Angewandte Chemie, 49(31):5301-5304 (2010). "Uniform amplification of phage with different growth characteristics in individual compartments consisting of monodisperse droplets."
Derda et al., Journal of the American Chemical Society, 132(4):1289-1295 (2010). "High-throughput discovery of synthetic surfaces that support proliferation of pluripotent cells."
Derda et al., Molecules, 16(2):1776-1803 (2011). "Diversity of phage-displayed libraries of peptides during planning and amplification."
Doi et al., FEBS Letters, 457(2):227-230 (1999). "STABLE: protein-DNA fusion system for screening of combinatorial protein libraries in vitro."
Granieri et al., Chemistry & Biology, 17(3):229-235 (2010. "High-throughput screening of enzymes by retroviral display using droplet-based microfluidics."
Ionnolo et al., Biological Chemistry, 378(6):517-521 (1997). "Construction, exploitation and evolution of a new peptide library displayed at high density by fusion to the major coat protein of filamentous phage."
Petrenko et al., Protein Engineering, 9(9):797-801 (1996). "A library of organic landscapes on filamentous phage."
Rodi et al., Journal of Molecular Biology, 322(5):1039-1052 (2002). "Quantitative assessment of peptide sequence diversity in M13 combinatorial peptide phage display libraries."
Zhou et al., Journal of the American Chemical Society, 124(4):538-543 (2002). "A novel strategy by the action of ricin that connects phenotype and genotype without loss of the diversity of libraries."
Amstutz et al., "In vitro display technologies: novel developments and applications." Curr. Opin. Biotechnol. 12:400-405 (2001).
Anna et al., "Formation of dispersions using 'flow focusing' in microchannels." Appl. Phys. Lett. 82(3):364-366 (2003).
Arap et al., "Steps toward mapping the human vasculature by phage display." Nat. Med. 8(2):121-127 (2002).
Boder et al., "Yeast surface display for screening combinatorial polypeptide libraries." Nat. Biotechnol. 15(6):553-557 (1997).
Breaker et al., "Emergence of a replicating species from an in vitro RNA evolution reaction." PNAS 91 (13):6093-6097 (1994).
Brekke et al., "New technologies in therapeutic antibody development" Curr Opin. Pharmacol. 3(5):544-550 (2003).
Brown, "New approaches for cell-specific targeting: identification of cell-selective peptides from combinatorial libraries." Curr. Opin. Chem. Biol. 4(1):16-21 (2000).
Cwirla et al., "Peptides on phage: a vast library of peptides for identifying ligands." PNAS 87:6378-6382 (1990).
Devlin et al., "Random peptide libraries: a source of specific protein binding molecules." Science 249(4967):404-406 (1990).
Ganan-Calvo, "Generation of steady liquid microthreads and micron-sized monodispersed sprays in gas streams." Phys Rev Lett 80(2):285-288 (1998).
Ganan-Calvo et al., "Perfectly monodisperse microbubbling by capillary flow focusing." Phys Rev Lett 87(27 Pt. 1):274501 (2001).
Garstecki et al., "Mechanism for flow-rate controlled breakup in confined geometries: a route to monodisperse emulsions." Phys. Rev. Lett. 94(16)1 64501 (2005).
Ghadessy et al. "Directed evolution of polymerase function by compartmentalized self-replication." PNAS 98(8): 4552-4557 (2001).
Griffiths et al., "Miniaturising the laboratory in emulsion droplets." Trends in Biotechnology 24(9):395-402 (2006).
Halpin et al., "DNA display II. Genetic manipulation of combinatorial chemistry libraries for small-molecule evolution." PLoS Biol. 2:1022-1030 (2004).
Hanes et al., "In vitro selection and evolution of functional proteins by using ribosome display." PNAS 94:4937-4942 (1997).
Holtze et al. "Biocompatible surfactants for water-in-fluorocarbon emulsions." Lab Chip 8(10):1632-1639 (2008).
Iannolo et al., "Construction, exploitation and evolution of a new peptide library displayed at high density by fusion to the major coat protein of filamentous phage." Biol. Chem. 378:517-521 (1997).
Kehoe et al., "Filamentous phage display in the new millennium." Chem. Rev. 105(11):4056-4072 (2005).
Kiss et al. "Phage ESCape: An emulsion-based approach for the selection of recombinant phage display antibodies." Journal of Immunological Methods 367: 17-26 (2011).
Rodi et al., "One from col. A and two from col. B: the benefits of phage display in molecular-recognition studies." Curr. Opin. Chem. Biol. 6(1):92-96 (2001).
Smith, "Filamentous fusion phage: novel expression vectors that display cloned antigens on the virion surface." Science 228(4705):1315-1317 (1985).
Tawfik et al., "Man-made cell-like compartments for molecular evolution." Nat. Biotechnol. 16:652-656 (1998).
Ullmann et al., "Characterization by in vitro complementation of a peptide corresponding to an operator-proximal segment of the beta-galactosidase structural gene of Escherichia coli." J. Mol. Biol. 24(2):339-343 (1967).
Williams et al. "Amplification of complex gene libraries by emulsion PCR." Nature Methods 3(7): 545-550 (2006).
Wittrup, "Protein engineering by cell-surface display." Curr. Opinion Biotechnol., 12(4):395-399 (2001).
Yonezawa et al., "DNA display for in vitro selection of diverse peptide libraries." Nucleic Acids Res. 31(19):e118 (2003).
Garstecki et al., "Formation of monodisperse bubbles in a microfluidic flow-focusing device." Appl. Phys. Lett 85 (13):2649-2651 (2004).
Li et al., "Simultaneous generation of droplets with different dimensions in parallel integrated microfluidic droplet generators," Soft Matter 4:258-262 (2008).

* cited by examiner start: $8 \times 10^7$ cells/mL, $3.3 \times 10^{-8}$ mL/droplet;
average per drople concentration: 2.6 cells per droplet final
droplet occupancy: ~100% of the drops are infected
global concentration: $1.5 \times 10^9$ cells/mL
per droplet concentration: $1.5 \times 10^9 \times 3.3 \times 10^{-8}$ = 50 cells/droplet FIG. 6A
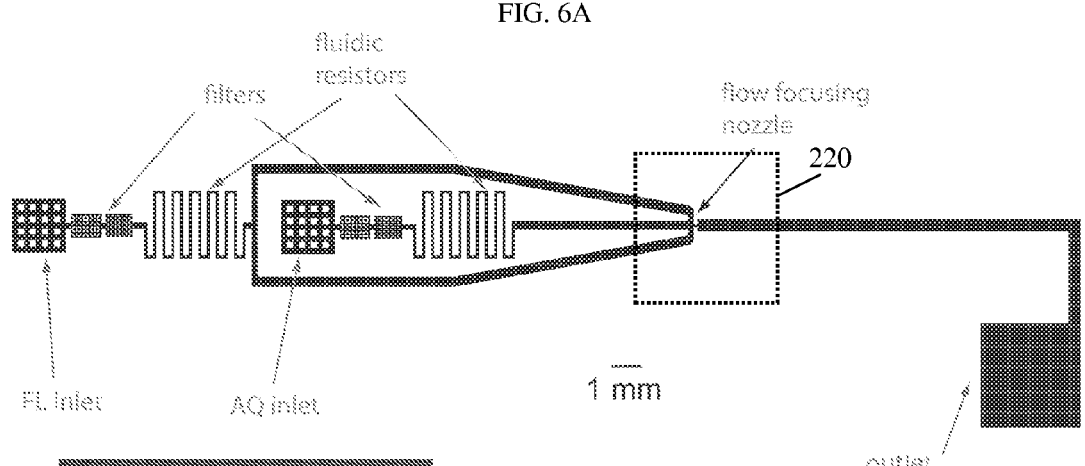
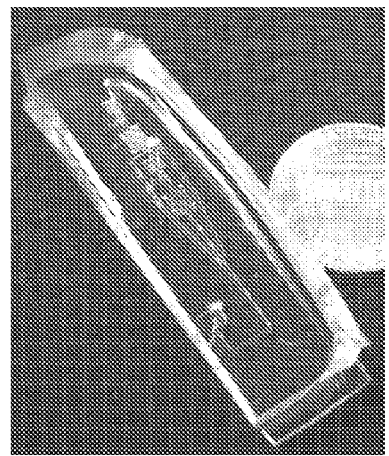
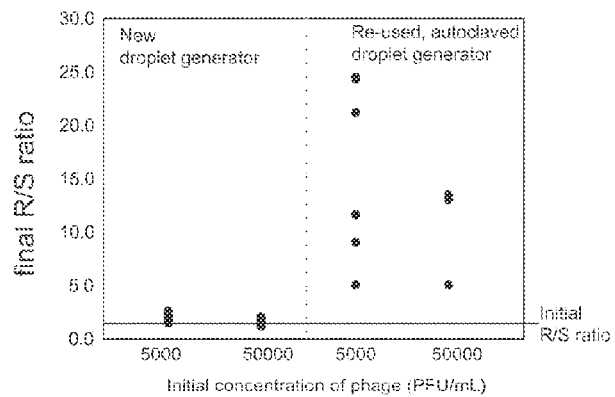
FIG. 6B
FIG. 6C

SYSTEMS AND METHODS FOR AMPLIFICATION AND PHAGE DISPLAY

CROSS REFERENCE TO RELATED APPLICATIONS

This application is a 35 U.S.C. §371 National Phase Entry Application of International Application No. PCT/US2011/039932 filed Jun. 10, 2011, which designates the U.S., and which claims benefit under 35 U.S.C. §119(e) of the U.S. Provisional Application No. 61/353,324, filed Jun. 10, 2010, the contents of which are incorporated herein by reference in their entireties.

GOVERNMENT SUPPORT

This invention was made with federal funding under Grant No. ES016665 awarded by the National Institutes of Health, Grant No. DMR-0820484 awarded by the National Science Foundation, and Grant No. W911NF-07-10647 awarded by the Defense Advanced Research Projects Agency. The U.S. government has certain rights in the invention.

FIELD OF INVENTION

The present invention generally relates to amplification of biological entities, for example, for phage display.

BACKGROUND

Phage display allows de novo selection of ligands that bind to a large range of targets from libraries of polypeptides of great diversity (e.g., greater than $10^9$ different polypeptides. Two important elements of selection in phage display makes phage display techniques of interest to researchers: (1) almost any peptide sequence can be displayed on the coat protein of phage by inserting a short DNA sequence into the genome of the phage and (2) bacteria infected by a phage displaying peptide produce multiple copies of this particular phage rapidly (e.g., amplification by ~$10^3$ every 20-60 min).

Rounds of selection and amplification make it possible to select peptides from a phage display library that can bind usefully to targets. Modifications of phage coat proteins, however, can influence the rates of infection of bacteria, the rates of assembly of the new phage particles, and/or the rates of phage production from infected bacteria. When phage with different rates of amplification compete for the same pool of bacteria, clones that replicate more rapidly capture an increasing fraction of the total pool of bacteria, thereby reducing the diversity of the phage display library during amplification and thus, the usefulness of such amplified libraries. Accordingly, improvements in phage display and other amplification techniques are needed.

SUMMARY OF THE INVENTION

The present invention generally relates to amplification of biological entities, for example, for phage display. The subject matter of the present invention involves, in some cases, interrelated products, alternative solutions to a particular problem, and/or a plurality of different uses of one or more systems and/or articles.

Embodiments of the present invention are based on, at least in part, the discovery of uniform amplification of phages with various growth or amplification rates in individual compartments, e.g., monodisperse droplets. The inventors have demonstrated that separating each individual phage clone with a different growth rate into any monodisperse individual droplets, e.g., generated by a microfluidic device, can overcome the problem of fast-replicating clones capturing a larger fraction of the total pool of bacteria than the slow-replicating ones, and thus maintain the diversity of the phage library. Thus, the inventors' findings provide methods of amplifying a library of diverse clones (e.g., phages and other biological entities) while maintaining the library diversity.

Accordingly, provided herein is a method of producing an amplified library of clones, the method comprising: (a) distributing a library of clones comprising a plurality of distinguishable replicable genetic package members into a plurality of monodisperse individual compartments such that substantially no more than one replicable genetic package member is contained in any individual compartment; and (b) amplifying the library of step (a) for a sufficient period of time such that each of the distinguishable members replicates to reach substantially the same copy number within the individual compartments; thereby maintaining diversity of the library of clones upon amplification. In some embodiments, each of the distinguishable members replicates to reach saturation, e.g., reaching a maximum copy number allowed in the individual compartments. Examples of the replicable genetic package members include, but are not limited to, viruses, eukaryotic cells, spores, yeast cells, bacterial cells, nucleic acid sequences, or recombinants thereof.

Some embodiments of the methods provided herein are applicable to various libraries of clones, including, but not limited to, phage display, yeast display, bacterial display, RNA display, DNA display, and ribosome display. In some embodiments, the library described herein can comprise at least about 100 distinguishable clones. In some embodiments, the library described herein can comprise at least about 1,000 distinguishable clones. In some embodiments, the library described herein can comprise at least about $10^6$ distinguishable clones. In some embodiments, the library described herein can comprise at least about $10^9$ distinguishable clones.

In certain embodiments, the methods provided herein can be applied to a phage library. For example, when the replicable genetic package is a virus (e.g., a bacteriophage), substantially each of the individual compartments further comprises at least one host cell (e.g., bacterial cells) capable of supporting replication of the replicable genetic package, wherein the number of host cells within each of the individual compartments is substantially the same. In some embodiments, substantially each of the individual compartments can further comprise at least ten host cells capable of supporting replication of the replicable genetic package.

Accordingly, another aspect provided herein is a method of producing an amplified library of phage clones, the method comprising: (a) distributing a library of phage clones comprising a plurality of distinguishable phage clones into a plurality of monodisperse individual compartments such that substantially no more than one phage clone is contained in any individual compartment, and wherein each of the individual compartments further comprises at least one bacterial cell; and (b) culturing the library of step (a) for a sufficient period of time such that the bacterial cells replicate substantially to the same number within the individual compartments, thereby producing substantially the same copy number of each phage clone within the individual compartments; thereby maintaining diversity of the library of phage clones upon amplification. In some embodiments, substantially each of the individual compartments can further comprise at least ten bacterial cells. In such embodiments, the bacterial cells within the individual compartments can replicate to reach growth saturation, e.g., reaching maximum density of growth. In some embodiments, after the bacterial cells have reached growth saturation, the culturing can be continued until substantially all the bacterial cells have been infected by a phage within the individual compartments, thereby producing substantially the same copy number of each phage clone within the individual compartments.

In some embodiments of any methods described herein, each of the individual compartments can further comprise growth or replication media containing substantially the same amounts of nutrients.

In some embodiments of any methods described herein, the method of producing an amplified library of clones further comprises the step of releasing the amplified distinguishable members within the individual compartments into one common fluid. Exemplary releasing methods include, without limitations, adding at least one destabilization agent into the amplified library of which clones are still contained in the individual compartments, diluting the at least one surfactant, and/or applying electric fields to the amplified library of which clones are still contained in the individual compartments.

In accordance with the invention, the monodisperse compartments enable substantially uniform amplification of clones. In some embodiments, the monodisperse compartments can have a size (e.g., an average diameter) of at least about 40 μm. In some embodiments, the monodisperse compartments can have a size (e.g., an average diameter) of about 20 μm to about 500 μm. In some embodiments, the monodisperse compartments can have a size (e.g., an average diameter) of no larger than 200 μm. In some embodiments, the monodisperse compartments can have a size (e.g., an average diameter) of about 40 μm to about 200 μm. In some embodiments, the monodisperse compartments can have a size (e.g., an average diameter) of about 40 μm to about 100 μm.

In certain embodiments, the individual compartments employed in the methods described herein are fluidic droplets. Accordingly, in some embodiments, a plurality of replicable genetic package members can be distributed into a plurality of fluidic droplets, e.g., using at least one microfluidic device. In particular embodiments, substantially no more than one phage clone is distributed into any individual fluidic droplets, e.g., using at least one microfluidic device.

In some embodiments of any methods described herein, the fluidic droplets can be suspended in a perfluorinated liquid and stabilized by at least one surfactant.

Another aspect provided herein is a library of phage clones, in which the copy number of each distinguishable phage clone is substantially the same. In some embodiments, the phage clones can be contained within individual compartments. In some embodiments, the phage clones can be released from the individual compartments (e.g., using the releasing methods described herein) into a common fluid.

In one aspect, the present invention is also directed to a method of producing an amplified library of viral clones. In one set of embodiments, the method includes acts of providing an initial library of replicable genetic packages having a first distribution of growth rates including a first mean and a first standard deviation, and amplifying the initial library of replicable genetic packages to produce an amplified library of replicable genetic packages having a second distribution of growth rates including a second mean and a second standard deviation. In some cases, the first mean and the second mean differ by no more than about 10% relative to the first mean and the first standard deviation and the second standard deviation differ by no more than about 10% relative to the first standard deviation.

In another set of embodiments, the method comprises acts of providing a first compartment having a first volume and a second compartment having a second volume, where the first compartment contains a first viral clone and the second compartment contains a second viral clone, and amplifying the first viral clone and the second viral clone such that the ratio of the number of first viral clone particles to the number of second viral clone particles after amplification is essentially equal to the volumetric ratio of the first volume to the second volume. In some cases, the first viral clone and the second viral clone growth rates differ by at least about 10% relative to the slower growth rate of the first and second viral clones.

The invention, in another aspect, is directed to an article. The article, according to one set of embodiments, includes a viral library comprising a plurality of distinguishable clones. In some cases, essentially each distinguishable clone is contained within discrete microfluidic droplets. In one embodiment, the microfluidic droplets have a distribution of volumes such that at least about 90% of the droplets have a volume that varies by no more than about 10% relative to the average volume of the droplets.

The article, in another set of embodiments, includes a phage display library comprising at least 10,000 distinguishable viral clones having varying growth rates. In some cases, the highest growth rate of the viral clones is at least 10 times greater than the slowest growth rate of the viral clones. In certain embodiments, essentially each of the distinguishable viral clones contains at least 10,000 copies.

Kits for producing an amplified library of clones are also described herein. In such embodiments, the kit comprises (a) a container comprising a library of clones, the library of clones comprising a plurality of distinguishable replicable genetic package members; and (b) at least one microfluidic device for generating monodisperse droplets. Non-limiting examples of replicable genetic package members include a virus, a eukaryotic cell, a spore, a yeast cell, a bacterial cell, a nucleic acid sequence, or a recombinant thereof.

In some embodiments, the kit further comprises at least one host cell capable of supporting replication of the replicable genetic package when the replicable genetic package is a virus. In one embodiment, the virus is a phage.

Accordingly, provided herein include kits for producing an amplified library of phage clones comprising (a) a container comprising a library of phage clones; (b) a container comprising a plurality of bacterial cells; and (c) at least one microfluidic device for generating monodisperse droplets.

In some embodiments, any kit described herein can further comprise one or more containers comprising at least one surfactant. In other embodiments, the kit can further comprise one or more containers comprising at least one perfluorinated liquid. In some embodiments, the kit can further comprise one or more containers comprising at least one destabilization agent. In additional embodiments, the kit can further comprise one or more containers comprising growth or replication media. One or more containers for collecting droplets produced from a provided microfluidic device can also be included in some embodiments of the kit. In some embodiments, the kit can further comprise at least one syringe, at least one tubing or a combination thereof. An instruction manual for producing the amplified library can also be provided with the kit.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2B shows an image of droplets generated in microchannels of a microfluidic system, according to one or more embodiments of the invention;

FIGS. 6A-6B show a schematic and a picture of an exemplary microfluidic device for generating droplets containing bacteria in such microchannels, respectively, according to one embodiment.

FIG. 6C shows a graph comparing efficiencies of the method described herein using a new droplet generator and a reused, autoclaved droplet generator.

DETAILED DESCRIPTION OF THE INVENTION

Figure 1A:
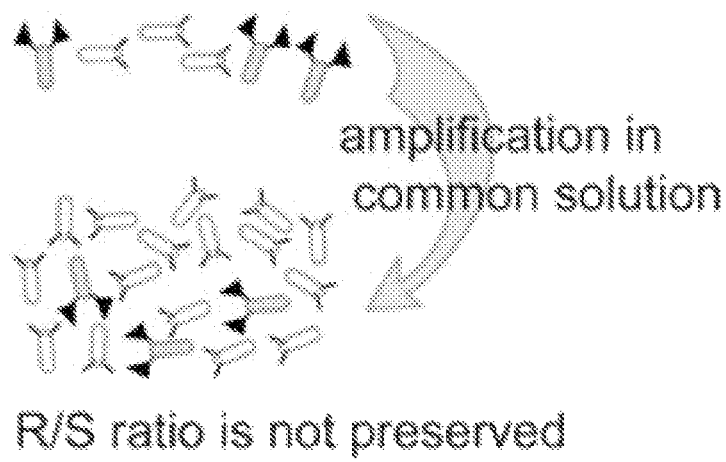
FIG. 1A is a schematic diagram illustrating amplification of two types of phage in the same solution.

The present invention generally relates to amplification of biological entities, for example, for phage display. Described herein are methods and kits for producing a library of amplified clones, e.g., phage clones, as well as the libraries of clones (e.g., phage clones) produced by the methods and/or kits described herein. In accordance with the invention, isolating members of a library of biological entities into individual monodisperse compartments allow uniform amplification of members with varying growth characteristics and thus preserve the diversity of the library.

In one aspect, members of a library of biological entities are encapsulated in separate compartments (e.g., in separate microfluidic droplets) and amplified. As a specific example, by putting members of a phage display library into microfluidic droplets such that essentially no droplet contains more than one distinguishable member of the library, the library can be amplified without any substantial changes in growth rates or population distributions, or other artifacts created due to differences in growth rates or amplification between different members of the library. In some cases, the volume of the compartments can be used to control the copy number of a biological entity during amplification. In certain cases, biological entities with different amplification rates can be amplified independently of each other. In some embodiments, the ratio of a rapidly amplifying biological entity to a slowly amplifying biological entity can be controlled. This can be advantageous, for example, in preserving diversity within a library by preventing rapidly amplifying biological entities from outcompeting slowly amplifying biological entities. For example, certain methods and systems of the invention can be useful in situations where preferential amplification of library members can present a problem.

One aspect of the invention is generally directed to amplifying a plurality of biological entities or replicable genetic packages (e.g., viruses, bacterial cells, mammalian cells, biomolecules, or the like) having a range of amplification rates. For example, in a phage display library, bacteria involved in phage display can be encapsulated in separate compartments (e.g., microfluidic droplets), and in some cases such that essentially no droplet contains more than one distinguishable member of the library. Surprisingly, such systems can be used to replicate or even amplify a library such as a phage display library without losing any diversity of the library, as is discussed below, a feature which has previously been unachievable with other amplification techniques known to those of ordinary skill in the art.

Generally, a library of biological entities includes a plurality of unique members having variations with respect to one or more properties (e.g., amplification rate). (Of course, the library can also contain non-unique or non-distinguishable members, e.g., a library can contain more than one copy of a particular member, although the library as a whole contains a plurality of unique members.) A specific example of a library of biological entities is a phage display library, where bacteriophages are used to infect bacteria such that the bacteria, once infected, will display proteins or other genes on their surfaces; by creating bacteriophages containing different genetic elements (e.g., different polypeptides), a library of such bacteriophages can be used as a phage display library. Other examples of such libraries of biological entities are discussed in detail below.

However, variations in amplification rate can be problematic for maintaining diversity within libraries such as phage display libraries. For example, in a system including biological entities that amplify relatively rapidly and biological entities that amplify relatively slowly, the rapidly amplified biological entities can outcompete the slowly amplified biological entities. In some cases, the difference in amplification rates can be such that the amplified system contains a smaller percentage or no longer contains any slowly amplified biological entities, i.e., the slowly-amplified entities are "outcompeted" by the faster-amplified entities during the amplification process.

In some embodiments, a library of biological entities (e.g., replicable genetic packages) can include biological entities having a distribution of different amplification rates (e.g., growth rates). In such embodiments, the amplification rates of the fastest-growing and the slowest-growing biological entities can differ by at least about 2-fold, at least about 3-fold, at least about 4-fold, at least about 5-fold, at least 7-fold, at least about 10-fold, at least about 20-fold, at least about 30-fold, at least about 40-fold, at least about 50-fold, at least about 75-fold, at least about 100-fold, at least about 250-fold, at least about 500-fold, at least about 1000-fold, at least about 2500-fold, at least about 5000-fold, at least about 7500-fold, at least about 10,000-fold or higher.

For example, in some cases, the amplification rates (e.g., growth rates) of at least a biological entity can differ from the fastest to the slowest growth rates by at least about 3%, at least about 5%, at least about 7%, at least about 10%, at least about 15%, at least about 20%, at least about 30%, at least about 50%, at least about 75%, at least about 100%, at least about 300%, at least about 500%, at least about 1,000%, at least about 3,000%, at least about 5,000%, at least about 10,000%, or even more. In some embodiments, such amplification rate ratio can be determined relative to the average of the amplification rates (e.g., growth rates) in the library of biological entities. In some instances, the amplification rates (e.g., growth rates) of a biological entity can differ by at least about 2 times, at least about 3 times, at least about 5 times, at least about 7 times, at least about 10 times, at least about 15 times, at least about 20 times, at least about 30 times, at least about 50 times, at least about 75 times, at least about 100 times, or even more, relative to an amplification rate of a different individual biological entity or an average amplification rate of a population of biological entities.

In certain cases, the mean and standard deviation of the growth rates of a library of biological entities having a distribution of different amplification rates can be determined or compared (e.g., before and after amplification) by any known methods in the art. For example, after amplification, the mean and/or the standard deviation can change by no more than about 25%, no more than about 20%, no more than about 15%, no more than about 10%, or no more than about 5%, taken relative to the values before amplification occurs. The amplification rates can be distributed in any suitable distribution, e.g., Gaussian.

In some cases, the amount of amplification can be to produce at least 10 copies of members of a library of biological entities, and in some cases, at least 100 copies, at least 1,000 copies, at least $10^5$ copies, at least $10^6$ copies, at least $10^7$ copies, at least $10^8$ copies, or at least $10^9$ copies. The total amount of amplification can be controlled by various factors, e.g., time duration allowed for amplification, beginning amount of biological entities, amount of supporting materials required for amplification, e.g., nutrients for cells, nucleotides for nucleic acid amplification, compartment size, and any combinations thereof.

The growth rates of bacteria (e.g., in a phage display library) or other biological entities in a library can be determined using routine techniques known to those of ordinary skill in the art. The specific technique used to determine the amplification rate (e.g., growth rate) can be a function of the particular application. For example, with respect to bacteria or bacteriophage, growth rates can be determined or estimated, for example, using cell counting techniques, hemocytometers, Coulter counters, spectroscopy, any methods for determination of plaque-forming units (PFU), e.g., plaque assays or the like. For determination of number of cells (e.g., eukaryotic cells), cell counting and other colorimetric assays known in the art (e.g., MTT assays) can be used. For concentration of nucleic acid concentrations, spectrometric methods, e.g., spectrometric measurement at 260 nm and other methods known in the art can be used.

In some embodiments, a library can include at least 10 distinguishable biological entities (for example, bacteria in a phage display library, or other libraries as is discussed herein), at least $10^2$ distinguishable biological entities, at least $10^3$ distinguishable biological entities, at least $10^4$ distinguishable biological entities, at least $10^5$ distinguishable biological entities, at least $10^6$ distinguishable biological entities, at least $10^7$ distinguishable biological entities, at least $10^8$ distinguishable biological entities, at least $10^9$ distinguishable biological entities, at least $10^{10}$ distinguishable biological entities, or even more.

Methods of Producing an Amplified Library

In accordance with the invention, separating each member of different biological entities, e.g., replicable genetic packages, into any monodisperse compartments can overcome selection of clones that amplify more rapidly than the rest of the library. Thus, one aspect provided herein is a method of producing an amplified library of clones, the method comprising: (a) distributing a library of clones comprising a plurality of distinguishable replicable genetic package members into a plurality of monodisperse individual compartments such that substantially no more than one replicable genetic package member is contained in any individual compartment; and (b) amplifying the library of step (a) for a sufficient period of time such that each of the distinguishable members replicates to reach substantially the same copy number within the individual compartments, thereby maintaining diversity of the library of clones upon amplification. In some embodiments, the method described herein can maintain at least about 70%, at least about 80%, at least about 90%, at least about 95%, at least about 96%, at least about 97%, at least about 98%, at least about 99% or higher, of the diversity of the library of clones. In some embodiments, the method described herein can maintain 100% diversity of the library of clones.

The term "distributing" as used herein generally refers to an act of separating or isolating a library of clones into a plurality of individual compartments, e.g., separate chambers or spaces with a defined volume, by any means known in the art depending on the types of individual compartments. For example, in some embodiments, when the individual compartments are microwells, a library of clones can be distributed into a plurality of individual compartments by diluting and pipetting the clones into a plurality of microwells. In some embodiments, when the individual compartments are fluidic droplets, a library of clones can be distributed into a plurality of individual compartments by encapsulating the clones into a plurality of fluidic droplets, e.g., using a microfluidic device.

In some embodiments, a library of clones or biological entities, such as a phage display library, having a distribution of bacteria or other appropriate replicable genetic package members can be amplified as follows. The members of the library can be encapsulated in separate compartments (e.g., in separate microfluidic droplets). In some embodiments, the members can be encapsulated such that essentially each droplet (or other compartment), on the average, contains one (or another predetermined number) member of the library. In some embodiments, substantially no more than one replicable genetic package member is contained in any individual compartment (e.g., any fluidic droplet). For example, the encapsulation efficiency can be initially chosen such that the average is much less than 1, e.g., such that most or essentially all of the droplets (or other compartments), e.g., at least 90%, at least 95%, at least 98%, at least 99% of the individual compartments (e.g., fluidic droplets) will either contain 0 or 1 member therein, while a very small (or essentially no) droplets will contain 2 or more different members therein. In one embodiment, no more than one replicable genetic package member is contained in any individual compartment (e.g., any fluidic droplet), i.e., 100% of the individual compartments (e.g., fluidic droplets) will either contain 0 or 1 member therein, while essentially no droplets will contain 2 or more different members therein. As such, the average number of members contained in an individual compartment (e.g., a fluidic droplet) can range from about 0.1 member per droplet to about 1.2 members per droplet, inclusive, or from about 0.5 member per droplet to about 1 member per droplet, inclusive. For example, the average number of member in a droplet can be set at 1 member per droplet, 0.9 members per droplet, 0.8 members per droplet, 0.7 members per droplet, 0.6 members per droplet, 0.5 members per droplet, 0.4 member per droplet, 0.3 member per droplet, 0.2 member per droplet, or 0.1 member per droplet. As discussed in detail below, certain techniques can also be used to identify droplets not containing any members therein, and optionally to remove those droplets from further analysis.

As used interchangeably herein, the terms "clones," "biological entities," and "replicable genetic packages" refer to a plurality of members characterized by one or more properties such as amplification rate or biological makeup (e.g., genetic information). Thus, the phrase "a library of clones" is a collection of members, including unique or distinguishable members having variations with respect to one or more properties (e.g., amplification rate, biological makeup). In some embodiments, a library of clones can further contain non-unique or non-distinguishable members, i.e., more than one copy of a particular member.

Techniques for encapsulating the members of the library in separate microfluidic droplets are discussed in detail below. In one non-limiting example technique, the encapsulation of members of a library into microfluidic droplets can be achieved using a microfluidic system, as discussed in detail below. For instance, a liquid containing cells such as bacteria can be introduced as a first fluid into a microfluidic system, and divided into a plurality of discrete fluidic droplets within a second fluid (typically immiscible with the first fluid) using flow-focusing techniques, stirring, pipetting, or other techniques such as those described in detail below. In certain embodiments, as discussed below, the droplets have essentially the same size or same volume (i.e., monodisperse).

The use of microfluidic droplets or other compartment systems are advantageous to the amplification of phage display libraries or other libraries of biological entities. Because essentially each member of the library is contained in a separate compartment or droplet, free from other members of the library, essentially each member of the library can be amplified free of competition or influences by other members of the library. Thus, even if different members of the library exhibit different growth rates, because essentially each member can be grown in separate compartments or droplets, free of any substantial competition from other members of the libraries, essentially each of the droplets or compartments will contain identical (or nearly identical) clones of that original member, without other members present (which could "crowd out" slower-growing or slower-amplifying members due to competition). Moreover, since essentially each member is isolated from other members, even though the members can grow at different rates, the final copy number of members present in essentially each droplet or compartment, after amplification, can be controlled to be essentially the same copy number, for example, in a system where each droplet or compartment has essentially the same size, essentially the same volume, essentially the same amount or concentration of nutrients (e.g., essentially the same amount of a growth-limited nutrient), and/or is subjected to essentially the same amount of amplification time, or the like. Examples of nutrients include, for example, a hormone, a vitamin, oxygen, glucose, an amino acid, a cofactor, a growth factor, or the like. An ordinary artisan will readily be able to determine nutrients required for different biological entities (e.g., bacterial or eukaryotic cells or viruses).

As another example, in some embodiments, the biological entities (e.g., replicable genetic packages) contained within the droplets (or other compartments) can be amplified for a period of time sufficient for substantially all of the members of the library to reach saturation within the droplets. In some embodiments, the biological entities contained with the droplets (or other compartments) can be amplified for a period of time sufficient for at least about 90% of the members of the library, including at least about 95%, at least about 98%, at least about 99% of the members of the library, to reach saturation within the droplets. In one embodiment, the biological entities contained with the droplets (or other compartments) can be amplified for a period of time sufficient for 100% of the members of the library to reach saturation within the droplets. In such embodiments, the amount of time for 100% of the biological entities to reach saturation depends on the slowest-growing biological entities (e.g., a phage with the slowest infection rate). The amount of time for amplifying the biological entities to reach saturation within the droplets can vary upon various factors such as amplification rates of different biological entities, amplification condition, and/or droplet size. The amount of time to reach saturation can thus vary from minutes to hours to days. For example, phage and/or bacterial cells can be amplified or incubated to reach growth saturation (e.g., stationary phase or a plateau) within droplets (e.g., at a controlled temperature between about room temperature and about 37° C.) for any hours, e.g., at least about 1 hour, at least about 2 hours, at least about 3 hours, at least about 4 hours, at least about 5 hours, at least about 6 hours, at least about 7 hours, at least about 8 hours, at least about 12 hours, at least about 24 hours, or longer. Eukaryotic cells (e.g., mammal cells) can be amplified or incubated to reach growth saturation within droplets (e.g., at a controlled temperature of about 37° C.) for any hours or days, e.g., at least about 12 hours, at least about 24 hours, at least about 2 days, at least about 3 days, at least about 4 days, at least about 5 days, at least about 6 days, at least about 7 days or longer. Nucleic acids contained within droplets can be subjected to a thermal cycler for amplification till reaching a saturation for any minutes or any hours, e.g., at least about 15 minutes, at least about 30 minutes, at least about 1 hour, at least about 2 hours, at least about 3 hours, at least about 4 hours, at least about 5 hours, at least about 6 hours, at least about 7 hours, at least about 8 hours or longer. One of skill in the art can determine or estimate the saturation time based on droplet sizes, and the art-recognized amplification kinetics of different biological entities (e.g., bacteria undergo exponential growth including a lag phase, an exponential (log) phase, a stationary phase, and a death phase. The readout of an exponential growth curve is known to those of skill in the art; for phage, the amplification rate can be ~1000 copies/~20 mins-~60 mins/bacterial cell.) In some embodiments, for phage amplification, amplification can be continued until host bacterial cells within the individual compartments have reached a stationary phase, and essentially all the replicated host bacterial cells are infected by a phage within the individual compartments such that essentially the same copy number of phages is produced within individual compartments. In such embodiments, for phage amplification, amplification can be continued for at least about 30 mins, at least about 1 hr, at least about 2 hours, at least about 3 hours, at least about 4 hours, at least about 5 hours, at least about 6 hours, or more after host bacterial cells within the individual compartments have reached a stationary phase.

In some embodiments, the amplification of the biological entities (e.g., replicable genetic packages) within the droplets or compartments can be determined with reference to copy number. As used herein, the "copy number" is the number of copies of a biological entity produced when a library is amplified. In some embodiments, the copy number of a relatively rapidly amplified biological entity is greater than the copy number of a relatively slowly amplified biological entity after amplification, and in some embodiments, such that the slowly amplified biological entity can suffer a decrease, or can even be unintentionally excluded from subsequent rounds of amplification. However, in certain embodiments of the invention, it has surprisingly been found that amplifying biological entities in separate compartments allows control over various aspects of the copy number of biological entities, i.e., ratio between biological entities, total copy number, and the like, typically essentially independently of any growth characteristics or properties of the biological entities themselves. In addition, as discussed herein, essentially each member of the library, contained within a separate droplet, can be grown to have the same final copy number, even if the members are amplified at different rates. Accordingly, in some embodiments, the biological entities (e.g., replicable genetic packages) contained within the monodisperse individual droplets (or other monodisperse individual compartments) can be amplified for a sufficient period of time such that each of the distinguishable members replicates to reach substantially the same copy number within the individual compartments. The phrase "substantially the same copy number within the individual compartments" as used herein refers to a difference in the copy number between any two individual compartments being no greater than 10%, no greater than 9%, no greater than 8%, no greater than 7%, no greater than 6%, no greater than 5%, no greater than 4%, no greater than 3%, no greater than 2%, no greater than 1%, no greater than 0.5%, no greater than 0.25%, no greater than 0.1%, no greater than 0.05%, no greater than 0.01% or lower. In some embodiments, the copy number within any individual compartment is no greater than 10%, no greater than 9%, no greater than 8%, no greater than 7%, no greater than 6%, no greater than 5%, no greater than 4%, no greater than 3%, no greater than 2%, no greater than 1%, no greater than 0.5%, no greater than 0.25%, no greater than 1%, no greater than 0.05%, no greater than 0.01% or lower, as compared to an average copy number within the individual compartments.

In some embodiments, copy numbers between a first biological entity and a second biological entity can be expressed as a ratio. For example, a library of members, such as a phage display library, can contain different populations of biological entities, which can have different growth rates in some cases. However, following amplification of the library of biological entities, the ratio of the first biological entity to the second biological entity can stay essentially the same as the original population, even if the biological entities have different growth rates.

In some embodiments, however, the ratio of the first biological entity to the second biological entity can differ. For example, the ratio can be higher or lower following amplification. It is a feature of certain embodiments of the invention that the ratio of the entities can be controlled before and after amplification, essentially independently of the actual growth rates of the first biological entity and the second biological entity. For example, by controlling the volume of the microfluidic droplets containing the first and second biological entities, the ratios of the number of biological entities can be independently controlled. Thus, as a specific non-limiting example, a first biological entity having a first growth rate and a second biological entity having a second growth rate can be amplified from a first ratio to a second different ratio, regardless of whether the first growth rate is the same, higher, or lower than the second growth rate. This control of amplification (e.g., growth) of the biological entities, independent of their growth rates, is an unexpected property. In some embodiments, suitable amplification (e.g., controlled copy numbers of biological entities in accordance with the droplet size/volume) can occur even if the actual growth rates and/or the ratios between the growth rates of the biological entities are unknown.

As mentioned, any of these scenarios (e.g., the population ratio of a first biological entity to a second biological entity being essentially the same, higher, or lower following amplification) can occur essentially independently of amplification or growth rates of the biological entities. As discussed herein, the copy number produced of a biological entity during amplification can be controlled by controlling any property that affects the ability of a biological entity to amplify. For example, the copy number can be controlled by controlling the droplet size (i.e., volume), the amount and/or presence and/or absence of nutrients, the amount of time that biological entity is allowed to amplify, or any combinations thereof.

As a specific example, the volume of the droplets or other compartments can be used, in some embodiments, to control the copy number of a biological entity. Thus, one way in which a plurality of biological entities can be amplified such that the copy number of essentially each biological entity is essentially monodisperse (i.e. essentially the same) would be to encapsulate the biological entities in monodisperse compartments. However, the use of monodisperse microfluidic droplets is described herein by way of example only, and in other embodiments, carrying essentially each member of a library forward through one or more rounds of amplification does not require that the compartments be monodisperse, and it should be understood that polydisperse compartments can also be used in certain embodiments.

After amplification, the biological entities (e.g., replicable genetic package members) can then be released from the compartments in some embodiments to create a final, amplified library of biological entities contained within a common fluid. Techniques for merging or releasing droplets are discussed in detail below. Such amplified libraries can then be used for any suitable purpose, e.g., any purpose in which a phage display library or other library of biological entities is needed. For example, a phage display library can be amplified and a portion of the amplified stored for later analysis; experiments involving phage display libraries can be replicated (e.g., in the same lab, or even in different labs); phage display or other libraries containing numerous different members can be analyzed for hard-to-identify or relatively slow-growing members without worrying about the loss of diversity which is typically expected during amplification, or the like.

As a specific example, in some cases, an amplified library such as a phage display library can be subjected to a selection process, where those members exhibiting a particular feature, for example, expression of a protein or binding to a target, are selected for additional amplification. For example, the selected biological entities can be individually encapsulated in compartments and amplified. The foregoing procedure can also be repeated until the library is sufficiently enriched with respect to the presence and/or magnitude of the feature, for example, based on some predetermined criteria. The entities can then be released from the compartments to create a final, amplified library of entities contained within a common fluid.

In some embodiments, a biological entity such as a bacteriophage can be encapsulated within a compartment. The compartment can be, for example, a droplet such as a microfluidic droplet, a well of a microtiter plate, or the like. The compartment can contain an aqueous solution and/or one or more nutrients. For example, the compartment can contain some or all of the nutrients necessary for the biological entity to amplify. In some cases, one or more nutrients is present in an excess amount, i.e., the amount of nutrients in the compartment exceeds the amount of nutrients that would be consumed by a biological entity amplifying prior to saturation within the compartment, where "saturation" means that the compartment can no longer contain greater numbers of biological entities (e.g., bacteriophages). In some embodiments, one or more of the nutrients are present in limiting quantities, e.g., such that the biological entity is amplified until one or more of the nutrients is exhausted, which can thereby limit any further growth of the biological entity. In some embodiments, the copy number of a biological entity is limited by the size of the compartment, i.e., the biological entity can be amplified until saturation of the biological entity within the compartment is reached. In some embodiments, the copy number of a biological entity within an individual compartment is limited by the availability of any supporting material for amplification (e.g., nutrients for cell growth, nucleotides for nucleic acid amplification) within the individual compartment.

In some embodiments, the biological entity can be a replicable genetic package. For example, the biological entity can be a replicable genetic package such as, without limitation, a virus (e.g, a bacteriophage (i.e., phage) or any other type of virus), a spore, a bacterial cell, a eukaryotic cell, a mammalian cell, a human cell, a cancer cell, a yeast cell, and a recombinant thereof. In some embodiments, the biological entity can be a replicable genetic package such as, without limitations, a nucleic acid sequence (i.e., DNA and/or RNA), a peptide, a protein, a polysaccharide, and a recombinant thereof. The term "recombinant" as used herein refers to any micro-organisms such as cells or viruses expressing a gene of interest that is produced by genetic engineering methods. In addition, "recombinant," as used herein, further describes a nucleic acid molecule, which, by virtue of its origin or manipulation, contains at least a portion of an exogenous or a heterologous polynucleotide. The term "recombinant" as used with respect to a protein or polypeptide, means a polypeptide produced by expression of a recombinant polynucleotide. The term "recombinant" as used with respect to a host cell means a host cell into which a recombinant polynucleotide has been introduced.

In some embodiments, more than one kind of biological entity can be used in the methods described herein. For example, the biological entity can be a virus-infected cell, for example, for phage display library techniques or the like. Accordingly, if the replicable genetic package is a virus, substantially each of the individual compartments, e.g., at least about 90%, including at least about 95%, at least about 98%, at least about 99% or even 100% of the individual compartments, can further comprise at least one host cell capable of supporting replication of the replicable genetic package, wherein the number of host cells within each of the individual compartments is substantially the same, e.g., at least about 90%, at least about 95%, at least about 98%, at least about 99%, or 100% of the individual compartments having the same number of host cells. In some embodiments, the substantially each of the individual compartments can comprise at least about 10 host cells, at least about 20 host cells, at least about 30 host cells, at least about 40 host cells, at least about 50 host cells, at least about 60 host cells, at least about 70 host cells, at least about 80 host cells, at least about 90 host cells, at least about 100 host cells, capable of supporting replication of the replicable genetic package. In such embodiments, the virus can be a bacteriophage and the host cells can be bacterial cells. In another example, the biological entity can be a cell having a plasmid inserted into it. In some embodiments, the biological entity can be a cell within a cell. If the replicable genetic package is a cell, the replicable genetic package can be eukaryotic or prokaryotic.

In a particular aspect, provided herein is also a method of producing an amplified library of phage clones, the method comprising: (a) distributing a library of phage clones comprising a plurality of distinguishable phage clones into a plurality of monodisperse individual compartments such that substantially no more than one phage clone is contained in any individual compartment, and wherein each of the individual compartments further comprises at least one bacterial cell; and (b) culturing the library of step (a) for a sufficient period of time such that the bacterial cells uniformly replicate and/or replicate essentially to the same number within the individual compartments, thereby producing substantially the same copy number of each distinguishable phage clone within the individual compartments; thereby maintaining diversity of the library of phage clones upon amplification. In some embodiments, the method described herein can maintain at least about 70%, at least about 80%, at least about 90%, at least about 95%, at least about 96%, at least about 97%, at least about 98%, at least about 99% or higher, of the diversity of the library of phage clones. In some embodiments, the method described herein can maintain 100% diversity of the library of phage clones.

As mentioned, certain aspects of the invention involve encapsulating members of a library, such as a phage display library, in a series of droplets such as microfluidic droplets. The members can be, e.g., bacteria, bacteriophages, other replicable genetic packages, or the like. In some embodiments, the droplets can be produced in a microfluidic device. The microfluidic device can be used for amplification, at least in certain cases. In some embodiments, amplification of the members can be performed within the microfluidic device, while other manipulations (e.g. selection) of biological entities (e.g., phage) can be performed in bulk solution, although in some instances, manipulations of biological entities can occur in a microfluidic device. Various example techniques for performing manipulations of droplets are discussed herein. In some cases, it can be desirable to combine a microfluidic device with other microfluidic components (e.g. a flow cytometer) for on-chip manipulation, quantification, or selection of drops. For example, in one set of embodiments, members of a library, such as a phage display library, are encapsulated in microfluidic droplets within a microfluidic droplet, such that most of the droplets contain 0 or 1 members of the library. In other cases, however, the droplets can contain 2 or more members. Optionally, the droplets can also be sorted, split, combined, fused, analyzed, etc., using techniques such as those discussed below.

Fluidic Droplets and Methods of Making the Same

It should be understood that the fluidic droplets can be formed using any suitable technique, not just within microfluidic devices. For example, the droplets can be formed by shaking or stirring a liquid to form individual droplets, creating a suspension or an emulsion containing individual droplets, or forming the droplets through pipetting techniques, needles, or the like. Other non-limiting examples of the creation of droplets are disclosed in U.S. patent application Ser. No. 11/024,228, filed Dec. 28, 2004, entitled "Method and Apparatus for Fluid Dispersion," by Stone, et al., published as U.S. Patent Application Publication No. 2005/0172476 on Aug. 11, 2005; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, International Patent Application No. PCT/US2008/007941, filed Jun. 26, 2008, entitled "Methods and Apparatus for Manipulation of Fluidic Species," each incorporated herein by reference.

As mentioned, in certain embodiments, fluidic droplets can be formed and/or combined, at a variety of scales, including microfluidic scales. In one set of embodiments, a fluidic stream is produced from a channel, where a cross-sectional dimension of the fluidic stream is smaller than that of the channel, for example, through the use of structural elements, other fluids, and/or applied external fields, etc. In some cases, a Taylor cone can be produced. In some cases, droplets produced using certain embodiments of the invention can be charged or substantially charged, which can allow their further manipulation, for instance, using applied external fields. Non-limiting examples of such manipulations include producing charged droplets, coalescing droplets (especially at the microscale), synchronizing droplet formation, aligning molecules within the droplet, etc.

In one aspect, the present invention allows the production or expulsion of a fluidic stream from a channel to occur in a manner that provides unique control over the fluidic stream and/or unique combinations of fluid or materials, as further described herein. As an example, a fluidic stream can be manipulated using one or more structural elements in or near its path of flow. As another example, a fluidic stream being produced or expelled from the channel can be contacted with another fluid in some fashion to manipulate the fluidic stream. As yet another example, an externally applied field (e.g., an electric and/or a magnetic field) can be generated proximate the channel outlet and/or proximate a fluidic stream to manipulate the fluidic stream. Combinations of any of these and/or other systems and techniques, e.g., as further described herein, are also contemplated in the present invention. Furthermore, the size of the fluidic stream, including droplet sizes in discontinuous streams, can be very precisely controlled in some instances.

In some cases, the fluidic stream can have an average cross-sectional dimension smaller than about 90% of an average cross-sectional dimension of the channel, and in certain embodiments, smaller than about 80%, about 70%, about 60%, about 50%, about 40%, or about 30% of the average cross-sectional dimension of the channel. In other embodiments, the fluidic stream can have an average cross-sectional dimension smaller than about 20%, about 10%, about 5%, about 3%, about 1%, about 0.5%, about 0.3%, about 0.1%, about 0.05%, about 0.03%, or about 0.01% of the average cross-sectional dimension of the channel. The fluidic stream, in some embodiments, can be produced on the microscale, e.g., using a microfluidic channel. For instance, the fluidic stream can have an average cross-sectional dimension of less than about 1 mm, less than about 500 microns, less than about 300 microns, or less than about 100 microns. In some cases, the fluidic stream can have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

In one set of embodiments, a structural element can be used to manipulate the fluidic stream in some fashion to produce a fluidic stream that has a cross-sectional dimension that is smaller than a cross-sectional dimension of a channel outlet that produces the fluid. In some cases, a fluidic stream can be produced where no cross-sectional dimension of the fluidic stream has a dimension that is larger than the smallest cross-sectional dimension of the channel outlet. A "structural element," as used herein, is a physical feature, in or proximate the channel, that is able to at least partially alter fluid flow from the channel. Examples of structural elements include dimensional restrictions, ridges, grooves, or the like. As used herein, a "dimensional restriction" is a structural element that is shaped to reduce a cross-sectional dimension of the fluidic stream. In some cases, the dimensional restriction is an annular orifice, but it can also take any of a variety of forms, for example, elongate, ovoid, square, triangular, or the like. The dimensional restriction is non-valved in preferred embodiments. Other examples of dimensional restrictions can be seen in International Patent Application No.

PCT/US03/20542, filed Jun. 30, 2003, entitled "Method and Apparatus for Fluid Dispersion," by Stone, et al., incorporated herein by reference in its entirety.

In some cases, the fluidic stream and/or the surrounding fluid has a mean cross-sectional dimension no smaller than 90% of the average cross-sectional dimension of the dimensional restriction, and in other embodiments, no smaller than 80%, 70%, 60%, 50%, 40%, or 30% of the average cross-sectional dimension of the dimensional restriction. This can be advantageous in certain cases in that a system of the invention can be operated over a range of fluid flowrates, and still produce a fluidic stream having the same, or approximately the same, size or cross-sectional dimension.

In another set of embodiments, one or more additional fluidic streams can be used to manipulate the fluidic stream in some fashion to produce a fluidic stream that has a cross-sectional dimension that is smaller than a cross-sectional dimension of a channel outlet that produces the fluid. The second fluid can be directed at the fluid and/or at the channel in such a way as to cause the fluidic stream produced by the channel to have a cross-sectional dimension smaller than a cross-sectional dimension of a channel outlet, and in some cases, such that no cross-sectional dimension of the fluidic stream has a dimension that is larger than the smallest cross-sectional dimension of the channel. In one embodiment, an additional fluid or fluids are directed in such a way as to surround or "sheath" the fluid being produced by the channel, reducing a cross-sectional dimension of the fluidic stream. The invention, in some cases, thus involves control over the average cross-sectional dimensions of the fluidic stream by control of the flowrate of a sheathing fluid, and/or control of the ratios of the flowrate of the fluidic stream relative to the sheathing fluid.

In yet another set of embodiments, an externally applied field (e.g., an electric and/or a magnetic field) can be generated proximate the channel outlet and/or proximate a fluidic stream to manipulate the fluidic stream, for example, to produce a fluidic stream that has a cross-sectional dimension that is smaller than a cross-sectional dimension of a channel outlet that produces the fluid. In one embodiment, the externally applied field includes a magnetic field. Techniques for producing suitable magnetic fields are known to those of ordinary skill in the art, for example, through the use of permanent magnets, electromagnets, or the like. In another embodiment, the externally applied field includes an electric field. The electric field can be generated from an electric field generator, i.e., a system able to produce an electric field, for example, directed substantially at the channel or at the channel outlet, and/or directed proximate the fluidic stream exiting the channel outlet. Techniques for producing a suitable electric field are known to those of ordinary skill in the art. For example, an electric field can be produced by applying a voltage drop across electrodes positioned proximate the channel outlet and/or fluidic stream.

The electric field generator can produce an AC field (i.e., one that varies periodically with respect to time, for example, sinusoidally, sawtooth, square, etc.), a DC field (i.e., one that is constant with respect to time), a pulsed field, etc. The electric field generator can be constructed and arranged to create an electric field within a fluid contained within a channel or a microfluidic channel. The electric field generator can be integral to or separate from the fluidic system containing the channel or microfluidic channel, according to some embodiments. As used herein, "integral" means that portions of the components integral to each other are joined in such a way that the components cannot be in manually separated from each other without cutting or breaking at least one of the components.

In one set of embodiments, electric charge can be created on a fluid surrounded by a liquid, which can cause the fluid to separate into individual or discrete droplets within the liquid. In some embodiments, the fluid and the liquid can be present in a channel, e.g., a microfluidic channel, or other constricted space that facilitates application of an electric field to the fluid (which can be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet can be large enough to cause the droplet to move within the liquid. In some cases, the electric force exerted on the fluidic droplet can be used to direct a desired motion of the droplet within the liquid, for example, to or within a channel or a microfluidic channel (e.g., as further described herein), etc.

Electric charge can be created in the fluid within the liquid using any suitable technique, for example, by placing the fluid within an electric field (which can be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. The liquid surrounding the fluid can have a conductivity less than that of the fluid. For instance, the liquid can be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid can be substantially hydrophilic, and the liquid surrounding the fluid can be substantially hydrophobic.

In some embodiments of the invention, systems and methods are provided for at least partially neutralizing an electric charge present on a fluidic droplet, for example, a fluidic droplet having an electric charge, as described above. For example, to at least partially neutralize the electric charge, the fluidic droplet can be passed through an electric field and/or brought near an electrode, e.g., using techniques such as those described herein. Upon exiting of the fluidic droplet from the electric field (i.e., such that the electric field no longer has a strength able to substantially affect the fluidic droplet), and/or other elimination of the electric field, the fluidic droplet can become electrically neutralized, and/or have a reduced electric charge.

In another set of embodiments, droplets of fluid can be created from a fluid surrounded by a liquid within a channel by altering the channel dimensions in a manner that is able to induce the fluid to form individual droplets. The channel can, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In other embodiments, internal obstructions can also be used to cause droplet formation to occur. For instance, baffles, ridges, posts, or the like can be used to disrupt liquid flow in a manner that causes the fluid to coalesce into fluidic droplets.

In some cases, the channel dimensions can be altered with respect to time (for example, mechanically or electromechanically, pneumatically, etc.) in such a manner as to cause the formation of individual fluidic droplets to occur. For example, the channel can be mechanically contracted ("squeezed") to cause droplet formation, or a fluid stream can be mechanically disrupted to cause droplet formation, for example, through the use of moving baffles, rotating blades, or the like.

Various embodiments of the invention use a plurality or series of fluidic droplets. The fluidic droplets can be polydisperse (e.g., having a range of different sizes), or in some cases, the fluidic droplets can be monodisperse or substantially monodisperse, e.g., in some embodiments, having a homogenous distribution of diameters, for instance, such that no more than about 50%, about 30%, about 20%, about 10%, about 5%, about 3%, about 1%, about 0.03%, or about 0.01% of the droplets have an average diameter greater than about 50%, about 30%, about 20%, about 10%, about 5%, about 3%, about 1%, about 0.03%, or about 0.01% of the average diameter. In some embodiments, monodisperse compartments, e.g., fluidic droplets, can refer to compartments (e.g., fluidic droplets) of which at least about 90%, at least about 95%, at least about 98%, at least about 99% or higher have an average diameter within a range around an average diameter, e.g., having a deviation of ±~10%, ±~9%, ±~8%, ±~7%, ±~6%, ±~5%, ±~4%, ±~3%, ±~2%, ±~1%, ±~0.5%, ±~0.2%, ±0.1%, of the average diameter. In some embodiments, monodisperse compartments, e.g., fluidic droplets, can refer to compartments (e.g., fluidic droplets) of which at least about 90%, at least about 95%, at least about 98%, at least about 99% or higher have an average diameter within a range around the most frequently-occurring diameter (i.e., the "mode"), e.g., having a deviation of ±~10%, ±~9%, ±~8%, ±~7%, ±~6%, ±~5%, ±~4%, ±~3%, ±~2%, ±~1%, ±~0.5%, ±~0.2%, ±0.1%, of the most frequently-occurring diameter (i.e., the "mode"). By way of example only, for a population of compartments (e.g., fluidic droplets) having the most frequently-occurring diameter of 100 µm (i.e., a distribution with a mode of 100 µm), at least 90% of the droplets are within a size range between 90 µm and 110 µm. In another example, for a population of compartments (e.g., fluidic droplets) having an average diameter of 100 µm, at least 90% of the droplets are within a size range between 90 µm and 110 µm.

In some embodiments, the term "monodisperse" as used herein refers to compartments (e.g., fluidic droplets) of which at least about 90%, at least about 95%, at least about 98%, at least about 99% or higher have an average volume within a range around the most frequently-occurring volume (i.e., the "mode"), e.g., having a deviation of ±~10%, ±~9%, ±~8%, ±~7%, ±~6%, ±~5%, ±~4%, ±~3%, ±~2%, ±~1%, +~0.5%, ±~0.2%, ±0.1%, of the most frequently-occurring volume (i.e., the "mode"). In some embodiments, the term "monodisperse" as used herein refers to compartments (e.g., fluidic droplets) of which at least about 90%, at least about 95%, at least about 98%, at least about 99% or higher have an average volume within a range around the average volume, e.g., having a deviation of ±~10%, ±~9%, ±~8%, ±~7%, ±~6%, ±~5%, ±~4%, ±~3%, ±~2%, ±~1%, ±~0.5%, ±~0.2%, ±0.1%, of the average volume. By way of example only, for a population of compartments (e.g., fluidic droplets) having the most frequently-occurring volume of 5 nL/drop (i.e., a distribution with a mode of 5 nL/drop), at least 90% of the droplets are within a volume range between 4.5 nL/drop and 5.5 nL/drop. In another example, for a population of compartments (e.g., fluidic droplets) having an average volume of 5 nL/drop, at least 90% of the droplets are within a volume range between 4.5 nL/drop and 5.5 nL/drop.

As used herein, a "fluid" is given its ordinary meaning, i.e., a substance that tends to flow and to conform to the outline of its container. Typically, fluids are materials that are unable to withstand a static shear stress, and when a shear stress is applied, the fluid experiences a continuing and permanent distortion. Thus, the fluid can have, in some cases, any suitable viscosity that permits at least some flow of the fluid. Non-limiting examples of fluids include liquids and gases, but can also include free-flowing solid particles, viscoelastic fluids, and the like. If two or more fluids are present, each fluid can be independently selected among essentially any fluids (liquids, gases, and the like) by those of ordinary skill in the art, by considering the relationship between the fluids. The fluids can each be miscible or immiscible. For example, two fluids can be selected to be immiscible within the time frame of formation of a stream of fluids, or within the time frame of reaction or interaction.

A "droplet" or a "fluidic droplet," as used herein, is an isolated portion of a first fluid that is completely surrounded by a second fluid. In such embodiments, the first and the second fluid are immiscible. For example, the first fluid is an aqueous fluid and the second fluid comprises a perfluorinated liquid such that the first fluid in the form of droplets suspended in a perfluorinated liquid. In such embodiments, any fluidic droplets of the methods described herein can contain substantially no more than replicable genetic package member (e.g., a phage clone) as described herein. In some embodiments, substantially each of the individual fluidic droplets can further comprise at least one host cell (or at least ten host cells or more) capable of supporting replication of the replicable genetic package (e.g., a phage clone) as described herein. In some embodiments, each of the individual fluidic droplets can further comprise growth or replication media containing substantially the same amounts of nutrients as described herein. It is to be noted that a droplet is not necessarily spherical, but can assume other shapes as well, for example, depending on the external environment. In one embodiment, the droplet has a minimum cross-sectional dimension that is substantially equal to the largest dimension of the channel perpendicular to fluid flow in which the droplet is located. The average diameter of a droplet, in a non-spherical droplet, is the diameter of a perfect mathematical sphere having the same volume as the non-spherical droplet. In various embodiments of the methods described herein, the fluidic droplets are monodisperse as described herein. While the fluidic droplets can have substantially the same shape, they can also have different shapes, but with substantially the same volume.

The "average diameter" of a population of droplets (or other individual compartments), as used herein, is the arithmetic average of the diameters of the droplets. Those of ordinary skill in the art will be able to determine the average diameter of a population of droplets, for example, using laser light scattering or other known techniques. As non-limiting examples, the average diameter of a droplet can be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers. The average diameter of the droplet can also be at least about 1 micrometer, at least about 2 micrometers, at least about 3 micrometers, at least about 5 micrometers, at least about 10 micrometers, at least about 15 micrometers, or at least about 20 micrometers in certain cases. In some embodiments, a fluidic droplet can have a volume of between 1 picoliter and 1 microliter, between, 1 picoliter and 100 nanoliters, between 1 picoliter and 10 nanoliters, or between 1 picoliter and 1 nanoliter. In some embodiments, a fluidic droplet can have a volume of less than 1 microliter, less than 100 nanoliters, less than 10 nanoliters, less than 1 nanoliter, or less than 100 picoliters.

In various embodiments of the methods described herein, the monodisperse (or substantially monodisperse) compartments (e.g., fluidic droplets) can have an average diameter of at least about 40 micrometers, at least about 50 micrometers, at least about 60 micrometers, at least about 70 micrometers, at least about 80 micrometers, at least about 90 micrometers, at least about 100 micrometers, at least about 150 micrometers, at least about 200 micrometers, at least about 250 micrometers, at least about 300 micrometers, at least about 350 micrometers, at least about 400 micrometers or higher. In some embodiments, the monodisperse compartments (e.g., fluidic droplets) can have an average diameter ranging from about 20 micrometers to about 500 micrometers, from about 40 micrometers to about 400 micrometers, from about 45 micrometers to about 200 micrometers, or from about 50 micrometers to about 100 micrometers. In some embodiments, the monodisperse compartments can have an average diameter of no larger than 400 micrometers, no larger than 300 micrometer, no larger than 200 micrometers, no larger than 100 micrometers, no larger than 50 micrometers or lower.

Stated other way, in various embodiments of the methods described herein, the monodisperse (or substantially monodisperse) compartments (e.g., fluidic droplets) can have an average volume of at least about 25 picoliters, at least about 50 picoliters, at least about 100 picoliters, at least about 150 picoliters, at least about 200 picoliters, at least about 300 picoliters, at least about 400 picoliters, at least about 1 nanoliter, at least about 2 nanoliters, at least about 4 nanoliters, at least about 10 nanoliters, at least about 15 nanoliters, at least about 30 nanoliters or higher. In some embodiments, the monodisperse compartments (e.g., fluidic droplets) can have an average volume ranging from about 1 picoliter to about 100 nanoliters, from about 25 picoliters to about 50 nanoliters, from about 35 picoliters micrometers to about 2 nanoliters, or from about 30 picoliters to about 500 picoliters. In some embodiments, the monodisperse compartments can have an average volume of no larger than 50 nanoliters, no larger than 20 nanoliters, no larger than 5 nanoliters, no larger than 600 picoliters, no larger than 100 picoliters or lower. In some embodiments, the monodisperse compartments (e.g., fluidic droplets) can have an average volume up to about 1 microliter, up to about 2 microliters, up to about 5 microliters, up to about 10 microliters or higher.

Exemplary Microfluidic Devices for Making Droplets

In some, but not all embodiments, all components of the systems and methods described herein are microfluidic. "Microfluidic," as used herein, refers to a device, apparatus or system including at least one fluid channel having a cross-sectional dimension of less than 1 mm.

Microfluidic systems can also be provided in certain embodiments that are able to cause two or more droplets to fuse or coalesce into one droplet. Examples of embodiments in which two or more droplets are fused have been described above. The fluidic droplets can be fused together using any suitable technique, for example, as discussed in U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference. In one embodiment, two droplets can be given opposite electrical charges (i.e., positive and negative charges, not necessarily of the same magnitude), which can increase the electrical interaction of the two droplets such that fusion or coalescence of the droplets can occur. Electrical charges (positive or negative) can be imparted onto droplets through the use of Taylor cones, or through any other suitable techniques. For instance, an electric field can be imposed on a reactor containing the droplets, the droplets can be passed through a capacitor, a chemical reaction can occur to cause the droplets to become charged, flowing the droplets over a region with opposite wetting properties, etc.

The "cross-sectional dimension" of the channel is measured perpendicular to the direction of fluid flow. Most fluid channels in components of the invention have maximum cross-sectional dimensions less than about 2 mm, and in some cases, less than about 1 mm. In one set of embodiments, all fluid channels containing embodiments of the invention are microfluidic or have a largest cross sectional dimension of no more than about 2 mm or about 1 mm. In another embodiment, the fluid channels can be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than about 500 microns, less than about 200 microns, less than about 100 microns, less than about 50 microns, or less than about 25 microns.

The fluidic droplets are contained, according to one set of embodiments, within a channel, such as a microfluidic channel. A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel can be completely enclosed along its entire length with the exception of its inlet(s) and outlet(s).

The channel can be of any size, for example, having a largest dimension perpendicular to fluid flow of less than about 5 mm or about 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel can be chosen such that fluid is able to freely flow through the article or substrate. The dimensions of the channel can also be chosen, for example, to allow a certain volumetric or linear flowrate of fluid in the channel. Of course, the number of channels and the shape of the channels can be varied by any method known to those of ordinary skill in the art.

The applied electric field can induce a charge, or at least a partial charge, on a fluidic droplet surrounded by a liquid. In some cases, the fluid and the liquid can be present in a channel, microfluidic channel, or other constricted space that facilitates the electric field to be placed on the field, for example, by limiting movement of the fluid within the liquid. The fluid within the fluidic droplet and the liquid can be essentially immiscible, i.e., immiscible on a time scale of interest (e.g., the time it takes a fluidic droplet to flow through a particular system or device). In addition, the electric field can be readily activated or deactivated, applied to a certain number or percentage of the fluidic droplets, or the like. Furthermore, the coalescence of the fluidic droplets can occur at a specific, predetermined time, and/or location within a channel.

A variety of materials and methods can be used to form components of the system, according to one set of embodiments of the present invention. In some cases various materials selected lend themselves to various methods. For example, components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Angell, et al., Scientific American 248:44-55 (1983). In one embodiment, at least a portion of the system is formed of silicon by etching features in a silicon chip. Technology for precise and efficient fabrication of devices of the invention from silicon is known. In another embodiment that section (or other sections) can be formed of a polymer, and can be an elastomeric polymer, or polytetrafluoroethylene (PTFE; Teflon®), or the like.

Different components can be fabricated of different materials. For example, a base portion including a bottom wall and side walls can be fabricated from an opaque material such as silicon or PDMS, and a top portion can be fabricated from a transparent material such as glass or a transparent polymer, for observation and control of the fluidic process. Components can be coated so as to expose a desired chemical functionality to fluids that contact interior channel walls, where base supporting material does not have the precise, desired functionality. For example, components can be fabricated as illustrated, with interior channel walls coated with another material.

Material used to fabricate devices of the invention, or material used to coat interior walls of fluid channels, can desirably be selected from among those materials that will not adversely affect or be affected by fluid flowing through the device, e.g., material(s) that is chemically inert in the presence of fluids to be used within the device.

In one embodiment, components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid art that can be induced to solidify, or that spontaneously solidifies, into a solid capable of containing and transporting fluids contemplated for use in and with the network structure. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point; or a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Examples of silicone elastomers suitable for use according to the invention include those formed from precursors including the chlorosilanes such as methylchlorosilanes, ethylchlorosilanes, and phenylchlorosilanes, and the like.

Silicone polymers are preferred in one set of embodiments, for example, the silicone elastomer polydimethylsiloxane (PDMS). Exemplary polydimethylsiloxane polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, 65° C. to about 75° C. for exposure times of about, for example, 1 hour. Also, silicone polymers, such as PDMS, can be elastomeric and thus can be useful for forming very small features with relatively high aspect ratios, necessary in certain embodiments of the invention. Flexible (e.g. elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain at their surface chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in Duffy et al., Rapid Prototyping of Microfluidic Systems and Polydimethylsiloxane, Analytical Chemistry, Vol. 70, pages 474-480, 1998, incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, it is preferred that the substrate be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

In some embodiments described herein, at least one microfluidic device is used to generate monodisperse droplets comprising replicable genetic packages (e.g., phage clones). In some embodiments, at least one microfluidic device is used to generate monodisperse droplets comprising replicable genetic packages (e.g., phage clones) and host cells. In some embodiments, any microfluidic devices configured for flow focusing, i.e., a hydrodynamic technology comprising a continuous phase fluid (focusing or sheath fluid) surrounding a dispersed phase (focused or core fluid), where droplets break-off in the vicinity of at least one orifice through which both fluids are extruded. Various art-recognized microfluidic flow-focusing devices can be used for the methods described herein to generate monodisperse droplets, e.g., the one described in the U.S. Pat. Nos. 7,759,111; 7,708,949; U.S. Patent Application No.: US 2010/0022414; PCT Application No.: WO 2004/002627, and any other references cited herein.

In one embodiment, a microfluidic device comprising a flow-focusing configuration 220 (or a flow-focusing nozzle design) as shown in FIG. 2B is used for generating monodisperse droplets for the methods described herein. By way of example only, the flow-focusing nozzle of the microfluidic device includes a microfluidic interconnected region 200 (defined by side walls 202), an upstream portion 204 and a downstream portion 206, which can be further connected to an outlet not shown in FIG. 2B. Additionally, the flow-focusing nozzle includes a subject fluid channel 208 (defined by side walls 210) provided within the outer boundaries of the interconnected region 200. The subject fluid channel 208 has an outlet 212 between the upstream portion 204 and the downstream portion 206 of the interconnected region 200. The interconnected region 200 further includes a dimensionally-restricted section 214 formed by extensions 216 extending from the side walls 202 into the interconnected region. Any fluid flowing from the upstream portion 204 to the downstream portion 206 of the interconnected region must pass through dimensionally-restricted section 214, after which droplets are formed in the downstream portion 206. The outlet 212 of the subject fluid channel 208 is positioned upstream of the dimensionally-restricted section 214. In one embodiment illustrated in FIG. 2B, the downstream portion of the interconnected region 200 has a central axis 218, which is the same as the central axis of the subject fluid channel 208. Thus, the subject fluid channel is positioned to release a subject fluid (e.g., an aqueous fluid comprising replicable genetic package members) upstream of the dimensionally-restricted section, and in line with the dimensionally-restricted section. As shown in FIG. 2B, in one embodiment, the subject fluid channel 208 releases the subject fluid into an interior portion of interconnected region 200 (between the outlet 212 and the dimensionally-restricted section 214), wherein the subject fluid is surrounded at least in part by dispersing fluid(s) (e.g., a fluorous phase such as an organic phase comprising a perfluorinated liquid) in the interconnected region, but is not completely surrounded by the dispersing fluid(s) in the interconnected region.

In various embodiments of the flow-focusing nozzle described herein, the interconnected region can have a maximum cross-sectional dimension of less than 1 millimeter, less than 500 microns, less than 200 microns, less than 100 microns, less than 50 microns, less than 25 microns or lower.

In various embodiments of the flow-focusing nozzle described herein, the dimensionally-restricted section can have an orifice of any shape, including, without limitations, annular, elongated, ovoid, and square. The orifice can be shaped in any way that can cause the dispersing fluid(s) to surround and constrict the cross-sectional shape of the subject fluid. In some embodiments, the orifice of the dimensionally-restricted section can have a maximum cross-sectional dimension of less than 200 microns, less than 100 microns, less than 50 microns, less than 25 microns, less than 20 microns, less than 10 microns, less than 5 microns, less than 1 micron, less than 0.5 microns, less than 0.1 microns, less than 0.05 microns or lower. One of skill in the art can readily determine an appropriate orifice size based on the desired droplet size.

In addition to at least one flow-focusing nozzle, the microfluidic device can further comprises additional features, such as filters (e.g., to remove any debris larger than the orifice size of the dimensionally-restricted section) and obstruction elements (e.g., fluidic resistors), separate inlets for the subject fluid and the dispersing fluid, an outlet for the exit of the generated droplets. An exemplary microfluidic flow-focusing device for generating monodisperse droplets for the methods described herein is shown in FIG. 6A. An ordinary artisan can readily modify such design to increase the rate of droplet generation, e.g., by integrating a plurality of flow-focusing nozzle into the microfluidic device. Other designs of a flow-focusing nozzle disclosed in the PCT Application No.: WO 2004/002627, incorporated herein by reference in its entirety, can also be integrated into any microfluidic device described herein.

In operation, a pressure differential is created between the upstream portion and the downstream portion of the interconnected region to draw the flow of the fluids. In one embodiment, a syringe pump can be used to introduce the dispersing fluid and the subject fluid into the microfluidic device through the dimensionally-restricted section. The ratio of the flow rate of the subject fluid to the dispersing fluid can be less than 1:2, less than 1:5, less than 1:25, less than 1:50, less than 1:100, less than 1:250, less than 1:400 or lower. In some embodiments, the dispersing fluid can have a flow rate of between 0.1 mL/hr and 40 mL/hr, between 1 mL/hr and 20 m/hr or between 3 mL/hr and 10 mL/hr. In one embodiment, the flow rate of the dispersing fluid is about 6 mL/hr, and the ratio of the flow rate of the subject fluid to the dispersing fluid is 1:1.5, i.e., the flow rate of the subject fluid is about 4 mL/hr. The fluid flow rates can be adjusted based upon a number of factors including, but not limited to, channel dimensions, the orifice size of the flow-focusing nozzle, and number of droplets generated.

Subject fluid dispersion can be controlled by those of ordinary skill in the art, based on the teachings herein, as well as available teachings in the field of flow-focusing. Reference can be made, for example, to "Generation of Steady Liquid Microthreads and Micron-Sized Monodispersed Sprays and Gas Streams," Phys. Rev. Lett., 80:2, Jan. 12, 1998, Ganan-Calvo, as well as numerous other texts, for selection of fluids to carry out the purposes of the invention. Control of dispersing fluid flow rate, and ratio between the flow rates of dispersing and subject fluids, can be used to control subject fluid stream and/or dispersion size, and monodispersity versus polydispersity in fluid dispersions.

In some embodiments described herein, the subject fluid is an aqueous fluid comprising a plurality or a library of replicable genetic package members, e.g., viruses, eukaryotic cells, spores, yeast cells, bacterial cells, nucleic acid sequences or recombinants thereof, as described herein. In certain embodiments, the subject fluid is an aqueous fluid comprising a plurality or a library of phage clones, and a plurality of host cells, such as bacterial cells. In various embodiments, the aqueous fluid can be any growth media or replication media containing substantially the same amount of supporting materials (e.g., nutrients) required for replication of the replicable genetic package members and/or growth of the host cells.

In some embodiments described herein, the dispersing fluid can be any fluid that is immiscible with the aqueous fluid and chemically stable and inert, and allows formation of droplets, e.g., oils, organic fluids, and perfluorinated liquids. In one embodiment, the dispersing fluid is a perfluorinated liquid. The term "perfluorinated liquid" as used herein includes organic compounds in which all (or essentially all) of the hydrogen atoms are replaced with fluorine atoms. Representative perfluorinated liquids include, without limitations, cyclic and non-cyclic perfluoroalkanes, perfluoroamines, perfluoroethers, perfluorocycloamines, and any mixtures thereof. Specific representative perfluorinated liquids include the following: perfluoropentane, perfluorohexane, perfluoroheptane, perfluorooctane, perfluoromethylcyclohexane, perfluorotributyl amine, perfluorotriamyl amine, perfluoro-N-methylmorpholine, perfluoro-N-ethylmorpholine, perfluoroisopropyl morpholine, perfluoro-N-methylpyrrolidine, perfluoro-1,2-bis(trifluoromethyl) hexafluorocyclobutane, perfluoro-2-butyltetrahydrofuran, perfluorotriethylamine, perfluorodibutyl ether, and mixtures of these and other perfluorinated liquids. Commercially-available perfluorinated liquids can also be used as the dispersing fluid, for example, but not limited to, Fluorinert™ FCTM-43 Electronic Fluid, Fluorinert™ FCTM72 Electronic Fluid, Fluorinert™ FCTM-77 Electronic Fluid, Fluorinert™ FCTM-84 Electronic Fluid, Fluorinert™ FCTM87 Electronic Fluid, Performance Fluid™ PF-5060, Performance Fluid™ PF-5070, and Performance Fluid™ PF-5052. Some of these liquids are described in Fluorinert™ Electronic Fluids, product bulletin 98-0211-6086(212) NPI, issued February 1991, available from 3M Co., St. Paul, Minn. In one embodiment, the perfluorinated liquid used herein comprises perfluorocarbon (HFE7500, obtained from 3M).

In any embodiments described herein, the dispersing fluid additionally comprises at least one surfactant, e.g., to stabilize the generated droplets and prevent them from coalescing after they are formed. An exemplary surfactant for such use is a commercially-available EA surfactant obtained from RainDance Technologies (Lexington, Mass., USA), which is a PEG-PFPE ((polyethylene glycol)-perfluoropolyether) amphiphilic block copolymer. Additional examples of surfactants that can be added into the dispersing fluid will be discussed in the next section. The amount of at least one surfactant added into the dispersing fluid can vary with a number of factors, e.g., the selection of surfactants (e.g., chemical properties), and amplification conditions (e.g., temperatures, time duration, mechanical agitation). Accordingly, the amount of at least one surfactant present in the dispersing fluid can vary from about 0.1% to about 10%, from 0.5% to about 8%, or from about 1% to about 5%. One of skill in the art can determine optimum concentrations of surfactants used in the dispersing fluid, e.g., by varying the concentrations of the selected surfactant under various amplification conditions and monitoring the stability of the droplets (e.g., droplet coalescence).

The dispersing fluid and the subject fluid can be introduced to the microfluidic device at the same time or in a pre-determined order. In one embodiment, the dispersing fluid can be introduced into the microfluidic device before the subject fluid. Such order of fluid introduction can minimize the interaction of replicable genetic packages and/or host cells (e.g., phages and bacterial cells) and thus minimize the possibility of the first burst of the progeny occurring (e.g., phage progeny) prior to the separation of all replicable genetic package members (e.g., phages) into individual monodisperse droplets.

The generated droplets comprising replicable genetic packages (and in some embodiments further comprising host cells) can then be subjected to amplification conditions (e.g., nucleic acid amplification) or culturing conditions (e.g., growth of virus-infected bacterial cells). In some embodiments, the amplification or culturing conditions can be carried out in the same or a different microfluidic device. In some embodiments, the amplification or culturing conditions can be carried out by any well-known methods known in the art. For example, the generated droplets can be collected from the outlet of the microfluidic device into a container containing a dispersing fluid comprising at least one surfactant (e.g., to prevent coalescence of drops upon contact with the surface of the container). Such dispersing fluid composition can be same as the one used in the microfluidic device, or it can be different. The collected droplets can then be subjected to appropriate conditions for amplification or cell growth. In the example of phage amplification, the collected droplets can be placed in a temperature-controlled shaker (e.g., a temperature set at about 36° C.-37° C.) for a sufficient period of time such that the bacterial cells uniformly replicate to reach growth saturation within the individual compartments.

In another aspect, the invention relates to systems and methods for splitting a fluidic droplet into two or more droplets. The two or more droplets created by splitting the original fluidic droplet can each be substantially the same shape and/or size, or the two or more droplets can have different shapes and/or sizes, depending on the conditions used to split the original fluidic droplet. In many cases, the conditions used to split the original fluidic droplet can be controlled in some fashion, for example, manually or automatically. In some cases, each droplet in a plurality or series of fluidic droplets can be independently controlled. Methods and devices described in the PCT Application No.: WO 2004/002627 (e.g., various obstructions placed in a fluid channel) can be used for splitting a fluidic droplet into two or more droplets.

According to one set of embodiments, a fluidic droplet can be split using an applied electric field. The electric field can be an AC field, a DC field, etc. The fluidic droplet, in this embodiment, can have a greater electrical conductivity than the surrounding liquid, and, in some cases, the fluidic droplet can be neutrally charged. In some embodiments, the droplets produced from the original fluidic droplet are of approximately equal shape and/or size. In some embodiments, the electric charge on the surface of the fluidic droplet can also experience a force due to the applied electric field, which causes charges having opposite polarities to migrate in opposite directions. The charge migration can, in some cases, cause the drop to be pulled apart into two separate fluidic droplets. Examples of splitting a fluidic droplet into two droplets are described in International Patent Application Serial No. PCT/US2004/010903, filed Apr. 9, 2004 by Link, et al.; U.S. Provisional Patent Application Ser. No. 60/498,091, filed Aug. 27, 2003, by Link, et. al.; and International Patent Application Serial No. PCT/US03/20542, filed Jun. 30, 2003 by Stone, et al., published as WO 2004/002627 on Jan. 8, 2004, each incorporated herein by reference.

In one set of embodiments, a fluid can be injected into a fluidic droplet, which can cause mixing of the injected fluid with the other fluids within the fluidic droplet to occur. The fluid can be microinjected into the fluidic droplet in some cases, e.g., using a microneedle or other such device. In other cases, the fluid can be injected directly into a fluidic droplet using a fluidic channel as the fluidic droplet comes into contact with the fluidic channel. Other examples of fluidic mixing in droplets are described in International Patent Application Serial No. PCT/US2004/010903, filed Apr. 9, 2004 by Link, et al., incorporated herein by reference.

In still another aspect, the invention provides systems and methods for screening or sorting fluidic droplets in a liquid, and in some cases, at relatively high rates. For example, a characteristic of a droplet can be sensed and/or determined in some fashion (e.g., as further described below), then the droplet can be directed towards a particular region of the device, for example, for sorting or screening purposes.

In some embodiments, a characteristic of a fluidic droplet can be sensed and/or determined in some fashion, for example, as described herein (e.g., fluorescence of the fluidic droplet can be determined), and, in response, an electric field can be applied or removed from the fluidic droplet to direct the fluidic droplet to a particular region (e.g. a channel). In some cases, high sorting speeds can be achievable using certain systems and methods of the invention.

In another set of embodiments, a fluidic droplet can be sorted or steered by inducing a dipole in the fluidic droplet (which can be initially charged or uncharged), and sorting or steering the droplet using an applied electric field.

In other embodiments, however, the fluidic droplets can be screened or sorted within a fluidic system of the invention by altering the flow of the liquid containing the droplets. For instance, in one set of embodiments, a fluidic droplet can be steered or sorted by directing the liquid surrounding the fluidic droplet into a first channel, a second channel, etc.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Non-limiting examples of devices able to cause the expansion and/or contraction of a liquid reservoir include pistons and piezoelectric components. In some cases, piezoelectric components can be particularly useful due to their relatively rapid response times, e.g., in response to an electrical signal.

The following documents are incorporated herein by reference: U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; priority to International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; U.S. patent application Ser. No. 09/004,583, filed Jan. 8, 1998, entitled "Method of Forming Articles Including Waveguides via Capillary Micromolding and Microtransfer Molding," by Kim, et al., now U.S. Pat. No. 6,355,198, issued Mar. 12, 2002; International Patent Application No. PCT/US01/16973, filed Can 25, 2001, entitled "Microfluidic Systems including Three-Dimensionally Arrayed Channel Networks," by Anderson, et al., published as WO 01/89787 on Nov. 29, 2001; S. Provisional Patent Application Ser. No. 60/392,195, filed Jun. 28, 2002, entitled "Multiphase Microfluidic System and Method," by Stone, et al.; U.S. Provisional Patent Application Ser. No. 60/424,042, filed Nov. 5, 2002, entitled "Method and Apparatus for Fluid Dispersion," by Link, et al.; U.S. Provisional Patent Application Ser. No. 60/461,954, filed Apr. 10, 2003, entitled "Formation and Control of Fluidic Species," by Link, et al.; International Patent Application No. PCT/US03/20542, filed Jun. 30, 2003, entitled "Method and Apparatus for Fluid Dispersion," by Stone, et al., published as WO 2004/002627 on Jan. 8, 2004; U.S. Provisional Patent Application Ser. No. 60/498,091, filed Aug. 27, 2003, entitled "Electronic Control of Fluidic Species," by Link, et al.; International Patent Application No. PCT/US2004/010903, filed Apr. 9, 2004, entitled "Formation and Control of Fluidic Species," by Link, et al., published as WO 2004/091763 on Oct. 28, 2004; International Patent Application No. PCT/US2004/027912, filed Aug. 27, 2004, entitled "Electronic Control of Fluidic Species," by Link, et al., published as WO 2005/021151 on Mar. 10, 2005; U.S. patent application Ser. No. 11/024,228, filed Dec. 28, 2004, entitled "Method and Apparatus for Fluid Dispersion," by Stone, et al., published as U.S. Patent Application Publication No. 2005-0172476 on Aug. 11, 2005; U.S. Provisional Patent Application Ser. No. 60/659,045, filed Mar. 4, 2005, entitled "Method and Apparatus for Forming Multiple Emulsions," by Weitz, et al.; U.S. Provisional Patent Application Ser. No. 60/659,046, filed Mar. 4, 2005, entitled "Systems and Methods of Forming Particles," by Garstecki, et al.; and U.S. patent application Ser. No. 11/246,911, filed Oct. 7, 2005, entitled "Formation and Control of Fluidic Species," by Link, et al.

Stabilization and Destabilization of Droplets in a Dispersing Fluid

The stability of droplets is essential for the methods described herein because maintaining each individual droplet as separate compartments for the replicable genetic package upon amplification prevents rapidly-growing replicable genetic package members from outcompeting the slow-growing replicable genetic package members. The individual droplets described herein can be stable for at least about 1 minute, at least about 5 minutes, at least about 10 minutes, at least about 20 minutes, at least about 30 minutes, at least about 40 minutes, at least about 1 hour, at least about 2 hours, at least about 6 hours, at least about 12 hours, at least about 1 day, at least about 1 week, at least about 1 month, or at least about 2 months, (e.g., at room temperatures or at a temperature of about 36-37 degrees Celsius and a pressure of 1 atm.) As used herein, the phrase "stability of droplets" means that at least about 90%, at least about 95%, at least about 98%, at least about 99% or higher of the droplets suspended in a dispersing fluid do not coalesce, e.g., to form larger droplets over these periods of time.

To prevent the coalescence of droplets upon amplification, the droplets can be dispersed in any immiscible fluid comprising a surfactant. As used herein, "surfactant" defines a molecule that, when combined with a first component defining a first phase (e.g., an aqueous phase), and a second component defining a second phase (e.g., a perfluorinated liquid), will facilitate assembly of separate first and second phases.

In one embodiment of the methods described herein, fluorosurfactants are used to stabilize aqueous droplets in a fluorophilic dispersing fluid (e.g., a perfluorinated liquid). The fluorosurfactants can include a fluorophilic tail soluble in a fluorophilic (e.g., fluorocarbon) dispersing phase, and a headgroup soluble in the internal phase of the droplets (e.g. aqueous phase inside the droplets described herein). The headgroup and the tail can be directly linked, or linked via a linking moiety. Various fluorosurfactants disclosed in the International Patent Application No.: WO 2008/021123 can be synthesized and used for stabilizing droplets in a fluorophilic dispersing fluid.

As used herein, a "fluorophilic" component comprises any fluorinated compound such as a linear, branched, cyclic, saturated, or unsaturated fluorinated hydrocarbon. The fluorophilic component can optionally include at least one heteroatom (e.g., in the backbone of the component). In some embodiments, the fluorophilic compound can be highly fluorinated, i.e., at least 30%, at least 50%, at least 70%, or at least 90% of the hydrogen atoms of the component are replaced by fluorine atoms. The fluorophilic component can comprise a fluorine to hydrogen ratio of, for example, at least 0.2:1, at least 0.5:1, at least 1:1, at least 2:1, at least 5:1, or at least 10:1. In some such embodiments, at least 30%, at least 50%, at least 70%, or at least 90% but less than 100% of the hydrogen atoms of the component are replaced by fluorine atoms. In other embodiments, the fluorophilic component is perfluorinated, i.e., the component contains fluorine atoms but contains no hydrogen atoms.

In some embodiments, the fluorophilic component of a surfactant is a fluorinated oligmer or polymer (i.e., a fluoropolymer). The fluoropolymer can include a (per)fluoropolyether chain, among other fluorinated polymers that are soluble in a fluorocarbon oil. The (per)fluoropolyether chain can comprise repeating units including, but not limited to, $-(C_nF_{2n}O)_x-$, where n is an integer, for example, $-(C_3F_6O)_x-$, $-(C_4F_8O)_x-$, $-(C_5F_{10}O)_x-$; $-(CF(CF_3)CF_2O)_x-$; $-(CF_2CF_2O)_x-$; $-(CF(CF_3)CF_2O)_x-$; $-(CF(CF_3)CONH-$; $-(CF_2(CF_2)_zCF_2O)_x-$, where z' is an integer; $-(CFLO)_x-$, where L=—F or —CF_3; and $-(CH_2CF_2CF_2O)_x-$. In some cases, $(C_nF_{2n+1}O)_x$ where n is an integer (for example, $-(CF_3O)_x-$, $-(C_2F_5O)_x-$, $-(C_3F_7O)x-$, etc.), is used as a terminal group and may not be polymerizable. In some cases, the (per)fluoropolyether chain can have the structure $(C_nF_mO)_x-$, where n and m are integers properly chosen to form a valid structure. Typically, x in the structures above is greater than or equal to 8. For example, x may be greater than or equal to 10, greater than or equal to 14, greater than or equal to 16, greater than or equal to 20, greater than or equal to 30, greater than or equal to 40, or greater than or equal to 50. In some embodiments, commercially-available perfluoropolyether, e.g., Krytox FS (H) (manufactured by DuPont) can also be used as a fluorophilic tail of a surfactant.

The surfactants described herein can have a headgroup soluble in an aqueous phase. In some embodiments, the surfactants can have a hydrophilic headgroup. In some embodiments, the hydrophilic component of a surfactant is a polymer (or oligomer). The polymer can include, for example, a polyether. The polyether chain can comprise repeating units including, but not limited to, $-(C_nH_{2n}O)_x-$, where n is an integer, for example, $-(C_3H_6O)_x-$, $-(C_4H_8O)_x-$ $-(C_5H_{10}O)_x-$; $-(C_2H_4O)_x-$; $-(C_3H_6O)_x-$, $-(C_4H_8O)_x-$, $-(C_5H_{10}O)_x-$; $-(CH(CH_3)CH_2O)_x-$; $-(CH_2CH_2O)_x-$; $-(CH(CH_3)CH_2O)_x-$; $-CH(CH_3)CONH-$; $-(CH_2(CH_2)_zCH_2O)_x-$, where z' is an integer; $-(CHLO)_x-$, where L=—H or —CH_3; or $-(CH_2CH_2CH_2O)_x-$. The polyether chain can include, in some embodiments, terminal groups such as $(C_nH_{2n+1}O)_x-$, where n is an integer, for example, $(CH_3O)_x-$, $(C_2H_5O)_x-$, $(C_3H_7O)_x-$, etc. In some embodiments, the hydrophilic component comprises polymethylene oxide, polyethylene oxide (or known as polyethylene glycol), polybutylene oxide, and/or polyTHF, and/or various polymers thereof. Typically, x in the hydrophilic structures above is greater than or equal to 1. For example, x may be greater than or equal to 5, greater than or equal to 10, greater than or equal to 14, greater than or equal to 16, greater than or equal to 20, greater than or equal to 30, greater than or equal to 40, or greater than or equal to 50. In other embodiments, a headgroup can include a sugar (e.g., glucose, glucosamine, and sorbitol). Other polar headgroups known to those of ordinary skill in the art are also be used in the surfactants described herein. In some embodiments, the hydrophilic headgroup of the surfactants can be non-ionic. In some embodiments, the headgroups soluble in an aqueous phase are also relatively biologically inert, i.e., the headgroups do not react with biological entities (e.g., replicable genetic package members and/or host cells) encapsulated inside droplets. Exemplary headgroups that are relatively biologically inert include, but are not limited to, dimorpholino phosphate (DMP) and polyethylene glycol (PEG). Other additional headgroups for such purpose are disclosed in the International Patent Application No.: WO 2008/021123, the content of which is incorporated herein by reference in its entirety.

Different geometries and/or configurations of the fluorosurfactants can be used for the methods described herein. For example, the fluorosurfactants can have a multi-block structure, e.g., a diblock structure comprising a headgroup and a fluorophilic tail, a tri-block structure comprising a headgroup and two fluorophilic tails, or in some embodiments, a headgroup connected to at least one fluorophilic tail via a linking moiety. In some embodiments, at least two diblock structures can be conjugated together by a linking moiety. In other embodiments, a fluorosurfactant can have a structure comprising more than one headgroups and at least one fluorophilic tail connected together by a linking moiety. The degree of the fluorosurfactant interaction with at least two immiscible phases (e.g., steric interaction) varies with different geometries and configurations of the fluorosurfactants.

In addition, to obtain long-term stabilized emulsions (i.e., a stable mixture of at least two immiscible liquids, e.g., individual droplets suspended in a perfluorinated liquid), certain ratios of molecular weights of the fluorophilic component to the headgroup component and/or thickness of the fluorophilic stabilizing layer can be required for steric stabilization of the droplets. In additional embodiments, fluorophilic components having large molecular weights can contribute to long term colloidal stabilization. These and other considerations for choosing appropriate components of fluorosurfactants and suitable mixtures of fluorsurfactants can be suitable for forming certain emulsions under various amplification conditions, for instance, emulsions comprising droplets having an average diameter in the micron or micrometer range subjected to agitation upon amplification.

In one embodiment, at least one surfactant employed in the methods herein has a diblock structure, e.g., an amphiphilic block copolymer. In such embodiments, the headgroup comprises PEG (polyethyglycol), and the fluorophilic tail comprises (PFPE) perfluoropolyether described herein. Poly(ethylene glyocol)s are well known and widely applied to "passivate" surfaces against non-specific adsorption of nucleic acids and proteins to solid surfaces, thus the use of PEG as the hydrophilic headgroups of the surfactant can provide more efficient shielding of the interfaces against the adsorption of biological entities (e.g., replicable genetic package members) as described herein.

Additional non-limiting examples of fluorosurfactants include the chemical structures designated by AEH12, AEH14, AEH19, AEH22, AEH23, AEH100, AEH101, AEH102, AEH103, AEH104, AEH105, AEH106, AEH107, and any of the fluorosurfactants as disclosed in the International Patent Application No.: WO 2008/021123, the content of which is incorporated herein by reference in its entirety.

In some embodiments, at least two surfactants can be dissolved in a dispersing phase and combined to assemble at the interface between the dispersing phase and droplets within an emulsion. By way of example only, one surfactant can provides colloidal stability of the emulsion. For example, KRYTOX® 157 FSL can be used for steric stabilization of the droplets. The other surfactant can be chosen to prevent adsorption of components such as chemicals, reactants, and biomolecules to the interfaces. For example, small amounts (<0.5% by weight) of a commercial fluorous surfactant that comprises a poly(ethylene glycol) group, such as ZONYL® (DuPont) FSN, can be used to sterically block the charges of the KRYTOX® surfactant.

After amplification, the amplified replicable genetic package members (e.g., phage-infected bacterial cells) within the individual droplets can be released into a common fluid, e.g., by merging or coalescing the droplets together using any of the art-recognized methods. Exemplary methods to release the amplified members into a common fluid include, without limitations, adding at least one destabilization agent or emulsion demulsifier into the droplet mixture; diluting the at least one surfactant (e.g., with additional dispersing fluid such as perfluorinated liquids); subjecting the droplet mixtures (emulsions) into electric fields; centrifuging the droplet mixtures (emulsions), or any combinations thereof. Exemplary destabilization agents include, but are not limited to, perfluorinated alcohol (e.g., 1H, 1H, 2H, 2H-perfluoro-1-octanol), water-saturated ether, silicone demulsifiers disclosed in the International Patent Application No.: WO 2007/149537; emulsion-breaking compositions disclosed in the U.S. Pat. No. 4,416,796; anhydride-based demulsifiers disclosed in the International Patent Application No.: WO 2009/148979; aqueous demulsifiers disclosed in the International Patent Application No.: WO 2000/013762; or any other droplet-destabilizing agents (demulsifiers) known in the art.

In some embodiments, the amplified members within the individual droplets can be released into a common fluid by diluting the emulsions or droplet mixtures (i.e., droplets suspended in a dispersing fluid, e.g., perfluorinated liquid, comprising at least one surfactant) with excess perfluorinated liquid (solvent), or washing the droplets with perfluorinated liquid (solvent) at least once, at least twice, at least three times, at least four times or more. In one embodiment, the perfluorinated liquid used for dilution herein can be the same as the dispersing fluid. In another embodiment, the perfluorinated liquid used for dilution herein can be different from the dispersing fluid. Emulsions are generally only stable at high concentrations of surfactant (~2%) in perfluorinated liquid (solvent). The droplets can coalesce much easier when the concentration of surfactant is low. For example, if the droplets, suspended in a perfluorinated dispersing fluid comprising at least one surfactant, are mixed with excess perfluorinated liquid (solvent), the concentration of the surfactant can drop below a critical level, and the droplets can coalesce over time. By way of example only, destabilization of droplets using such dilution method can be performed by pouring droplet emulsions into at least one separatory funnel or other similar apparatus, which can drain off the bottom perfluorinated liquid layer. More perfluorinated liquid can be added and then drained again, and this process can be repeated at least once, at least twice, at least three times, at least four times or more. This way, at least about 80%, at least about 90%, at least about 95%, at least about 98%, at least about 99% or 100%, of the surfactant can be washed off, and eventually the aqueous droplets can coalesce together to form a continuous layer that can be collected afterward, e.g., by draining.

Replicable Genetic Package Members and Libraries

In accordance with the invention, the methods described herein can be used to produce an amplified library of clones. The library can contain at least about 100 distinguishable clones, at least about 1000 distinguishable clones, at least about $10^5$ distinguishable clones, at least about $10^6$ distinguishable clones at least about $10^7$ distinguishable clones at least about $10^8$ distinguishable clones, at least about $10^9$ distinguishable clones or higher.

In certain aspects, as previously discussed, the display library is a phage display library. The phage library can contain at least about 100 distinguishable clones, at least about 1000 distinguishable clones, at least about $10^5$ distinguishable clones, at least about $10^6$ distinguishable clones at least about $10^7$ distinguishable clones at least about $10^8$ distinguishable clones, at least about $10^9$ distinguishable clones or higher. A phage display library can be formed, according to certain embodiments, by introducing nucleic acids encoding exogenous polypeptides to be displayed into the genome of a virus to form a fusion protein with an endogenous protein that is normally expressed from the outer surface of a bacterium to which the bacteriophage infects. Accordingly, libraries of phage clones produced by the methods of the invention, wherein the copy number of each distinguishable phage clone is substantially the same, are also provided herein. Techniques of forming phage display libraries are known to those of ordinary skill in the art, some of which are discussed below. Expression of the fusion protein, transport to the outer surface, and assembly results in display of exogenous polypeptides on the outer surface of the bacterium.

With respect to phage display libraries, as a specific example, in some embodiments, the genetic package used for a display library can be a bacteriophage. For example, the bacteriophage can be a filamentous phage such as M13, Fd, and/or Fl. In some cases, libraries encoding polypeptides to be displayed can be inserted into gIII or gVIII of these phages to form a fusion protein. See, e.g., Dower, WO 91/19818; Devlin, WO 91/18989; MacCafferty, WO 92/01047 (gene III); Huse, WO 92/06204; Kang, WO 92/18619 (gene VIII). In some embodiments, such a fusion protein comprises a signal sequence, usually from a secreted protein other than the phage coat protein, a polypeptide to be displayed and either the gene III or gene VIII protein or a fragment thereof. In some embodiments, other phages such as T7 or T4 can be used for a display library.

In some cases, exogenous coding sequences can be inserted at or near the N-terminus of gene III or gene VIII, although other insertion sites are possible. In some cases, a filamentous phage vector can be engineered to produce a second copy of either gene III or gene VIII. In such vectors, exogenous sequences can be inserted into only one of the two copies. Without wishing to be bound by any theory, expression of the other copy can dilute the proportion of fusion protein incorporated into phage particles and can be advantageous in reducing selection against polypeptides deleterious to phage growth.

In another variation, exogenous polypeptide sequences can be cloned into phagemid vectors that encode a phage coat protein and phage packaging sequences but which are not capable of replication. In some embodiments, phagemids can be transfected into cells and packaged by infection with helper phage. Use of phagemid system also can have the effect of diluting fusion proteins formed from coat protein and displayed polypeptide with wildtype copies of coat protein expressed from the helper phage. See, e.g., Garrard, WO 92/09690.

In some embodiments, eukaryotic viruses can be used to display polypeptides in an analogous manner. For example, display of human heregulin fused to gp70 of Moloney murine leukemia virus has been reported by Han, et al., *Proc. Natl. Acad. Sci. USA*, 92, 9747-9751 (1995).

In some embodiments, spores can also be used as replicable genetic packages. In this case, polypeptides are displayed from the outer surface of the spore. For example, spores from *B. subtilis* have been reported to be suitable. Sequences of coat proteins of these spores are provided, for example, by Donovan, et al., *J. Mol. Biol.*, 196, 1-10 (1987).

In some cases, cells can also be used as replicable genetic packages. In some examples, polypeptides to be displayed can be inserted into a gene encoding a cell protein that is expressed on the cells surface. Bacterial cells including, but not limited to, *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and *Escherichia coli* can be used. Details of outer surface proteins are discussed by Ladner, et al., U.S. Pat. No. 5,571,698, and Georgiou, et al., *Nature Biotechnology*, 15, 29-34 (1997) and references cited therein. For example, the lamB protein of *E. coli* can be suitable, in some embodiments.

In some embodiments, polypeptides typically displayed from replicable genetic packages can fall into a number of broad categories. For example, the library can be a library of short random or semi-random peptides. In some embodiments, a library of short peptides can be produced in which some or all of the positions are systematically varied for the different amino acids. In some cases, random peptide coding sequences can be formed by the cloning and expression of randomly-generated mixtures of oligonucleotides in appropriate recombinant vectors. See, e.g., Oliphant, et al., *Gene*, 44, 177-183 (1986).

In another example, a library can comprise variants of a starting framework protein. See Ladner, et al., U.S. Pat. No. 5,571,698. In this approach, a starting polypeptide which can be of substantial length is chosen and only selected positions are varied. In some embodiments, the nucleic acid encoding the starting polypeptide can be mutagenized by, for example, insertion of mutagenic cassette(s) or error-prone PCR.

In yet another example, a library can include antibody libraries. In some embodiments, an antibody library can be single or double chain. For example, a single chain antibody library can comprise the heavy or light chain of an antibody alone and/or the variable domain thereof. In some embodiments, the members of a single-chain antibody library can be formed from a fusion of heavy and light chain variable domains. In some instances, the fusion of heavy and light chain variable domains can be separated by a peptide spacer within a single contiguous protein. See e.g., Ladner, et al., WO 88/06630; or McCafferty, et al., WO 92/01047. In some embodiments, double-chain antibodies can be formed by noncovalent association of heavy and light chains or binding fragments thereof. In some cases, the diversity of antibody libraries can arise from obtaining antibody-encoding sequences from a natural source, such as a nonclonal population of immunized or unimmunized B cells. Alternatively, or additionally, diversity can be introduced by artificial mutagenesis as discussed for other proteins.

In some embodiments, nucleic acids encoding polypeptides to be displayed optionally flanked by spacers can be inserted into the genome of a replicable genetic package as discussed above by standard recombinant DNA techniques (see generally, Sambrooke, et al., *Molecular Cloning, A Laboratory Manual*, 2d ed., Cold Spring Harbor Laboratory Press, Cold Spring Harbor, N.Y., 1989, incorporated by reference herein). The nucleic acids can be ultimately expressed as polypeptides (with or without spacer or framework residues) fused to all or part of the outer surface protein of the replicable package. In some embodiments, a library can have a size of about $10^3$, about $10^4$, about $10^6$, about $10^7$, about $10^8$, or more members.

Double-chain antibody display libraries represent a species of the replicable genetic display libraries discussed above. Production of such libraries is described by, e.g., Dower, U.S. Pat. No. 5,427,908; Huse WO 92/06204; Huse, in Antibody Engineering, (Freeman 1992), Ch. 5; Kang, WO 92/18619; Winter, WO 92/20791; McCafferty, WO 92/01047; Hoogenboom WO 93/06213; Winter, et al., *Annu. Rev. Immunol.*, 12, 433-455 (1994); Hoogenboom, et al., *Immunological Reviews*, 130, 41-68 (1992); or Soderlind, et al., *Immunological Reviews*, 130, 109-124 (1992). In double-chain antibody libraries, one antibody chain can be fused to a phage coat protein, as is the case in single chain libraries. The partner antibody chain can be complexed with the first antibody chain, but the partner can not be directly linked to a phage coat protein. Either the heavy or light chain can be the chain fused to the coat protein. In some embodiments, whichever chain is not fused to the coat protein is the partner chain. In some embodiments, this arrangement can be achieved by incorporating nucleic acid segments encoding one antibody chain gene into, for example, either gIII or gVIII of a phage display vector to form a fusion protein comprising a signal sequence, an antibody chain, and a phage coat protein. In some embodiments, nucleic acid segments encoding the partner antibody chain can be inserted into the same vector as those encoding the first antibody chain. Optionally, heavy and light chains can be inserted into the same display vector linked to the same promoter and transcribed as a polycistronic message.

In another set of embodiments, nucleic acids encoding the partner antibody chain can be inserted into a separate vector (which can or can not be a phage vector). In this case, the two vectors can be expressed in the same cell (see, e.g., WO 92/20791). In some embodiments, the sequences encoding the partner chain can be inserted such that the partner chain is linked to a signal sequence, but is not fused to a phage coat protein. Both antibody chains can be expressed and exported to the periplasm of the cell where they can assemble and be incorporated into phage particles.

In some embodiments, antibody-encoding sequences can be obtained from lymphatic cells of a human or nonhuman animal. In some cases, the cells can have been immunized, in which case immunization can be performed in vivo before harvesting cells, or in vitro after harvesting cells, or both. In some embodiments, spleen cells of an immunized animal can be used as the source material. In some cases, immunization of humans can be possible only with certain antigens. In some embodiments, the number of different H chain genes and L chain genes in a spleen from an immunized animal can be about $10^6$, which can be assembled in $10^{12}$ potential combinations.

In some embodiments, rearranged immunoglobulin genes can be cloned from genomic DNA or mRNA. For the latter, mRNA can be extracted from the cells and cDNA can be prepared using reverse transcriptase and a primer (e.g., a poly dT oligonucleotide). Examples of primers for cloning antibody encoding sequences are discussed by Larick, et al., *Bio/Technology*, 7, 934 (1989), Danielsson & Borrebaceick, in *Antibody Engineering: A Practical Guide* (Freeman, New York, 1992), p. 89 and Huse, id.

In some embodiments, repertoires of antibody fragments can be constructed by combining amplified VH and VL sequences together. For example, light and heavy chains can be inserted into different vectors and the vectors combined in vitro (Hogrefe et al., Gene 128, 119-126 (1993)) or in vivo (Waterhouse et al., Nucl. Acids. Res. 21, 2265-66 (1993)). Alternatively, in some embodiments, the light and heavy chains can be cloned sequentially into the same vector (Barbas et al., Proc. Natl. Acad. Sci. USA 88, 7987-82 (1991)) or assembled together by PCR and then inserted into a vector (Clackson et al., Nature 352, 624-28 (1991)). In some cases, repertoires of heavy chains can also be combined with a single light chain or vice versa (Hoogenboom et al., J. Mol. Biol. 227, 381-88 (1992)).

Some exemplary vectors and procedures for cloning populations of heavy chain and light chain encoding sequences have been described by Huse, WO 92/06204. In some embodiments, diverse populations of sequences encoding Hc polypeptides can be cloned into M13IX30 and sequences encoding Lc polypeptides can be cloned into M13IX11. In some instances, the populations can inserted, for example, between the XhoI-SeeI or StuI restriction enzyme sites in M13IX30 or between the SacI-XbaI or EcoRV sites in M13IX11 (FIGS. 1A and B of Huse, respectively). Both vectors contain two pairs of MluI-HindIII restriction enzyme sites (FIGS. 1A and B of Huse) for joining together the Hc and Lc encoding sequences and their associated vector sequences. The two pairs can be symmetrically orientated about the cloning site so that only the vector proteins containing the sequences to be expressed are exactly combined into a single vector.

In some embodiments, the above strategy can be effected by the use of paired tags and receptors. A tag is typically a short peptide sequence and a receptor is any agent that shows specific but reversible binding for the tag and can be immobilized to a support. Suitable tag-receptor combinations include epitope and antibody; for example, many high affinity hexapeptide ligands are known for the anti-dynorphin mAb 32.39, (see Barrett, et al., *Neuropeptides*, 6, 113-120 (1985) and Cull, et al., *Proc. Natl. Acad. Sci. USA*, 89, 1865-1869 (1992)) and a variety of short peptides are known to bind the MAb 3E7 (Schatz, *Biotechnology*, 11, 1138-43 (1993)). Another combination of tag and antibody is described by Blanar & Rutter, *Science*, 256, 1014-1018 (1992).

Another example of a tag-receptor pair is the FLAG™ system (Kodak). The FLAG™ molecular tag includes of an eight amino acid FLAG peptide marker that is linked to the target binding moiety. A 24 base pair segment containing a FLAG coding sequence can be inserted adjacent to a nucleotide sequence that codes for the displayed polypeptide. The FLAG peptide includes an enterokinase recognition site that corresponds to the carboxy-terminal five amino acids. Capture moieties suitable for use with the FLAG peptide marker include, but are not limited to, antibodies Anti-FLAG M1, M2 and M5, which are commercially available.

Still other combinations of peptides and antibodies can be identified by conventional phage display methods. Further suitable combinations of peptide sequence and receptor include polyhistidine and metal chelate ligands containing $Ni^{2+}$ immobilized on agarose (see Hochuli in *Genetic Engineering: Principles and Methods* (ed. J K Setlow, Plenum Press, New York, Ch. 18, pp. 87-96) and maltose binding protein (Maina, et al., *Gene*, 74, 365-373 (1988)).

In some embodiments, a receptor can be labeled with biotin allowing the receptor to be immobilized to an avidin-coated support. Biotin labeling can be performed using the biotinylating enzyme, BirA (see, e.g., Schatz, *Biotechnology*, 11, 1138-43 (1993)).

In some embodiments, library members can be screened for binding to a target. The target can be any molecule or object of interest for which it is desired to identify binding partners. For example, the target can be an organism, such as a cell or virus, an organic molecule, a biomolecule (e.g., a protein, a nucleic acid, a polysaccharide, etc), a particle such as a quantum dot, a surface, etc.

The library members can be contacted with the target which can be labeled (e.g., with biotin) in such a manner that allows its immobilization. In some cases, binding can be allowed to proceed to equilibrium. The complexed targets and library members can be brought out of solution by addition of a solid phase to which the target bears affinity (e.g., an avidin-labeled solid phase can be used to immobilize biotin-labeled targets). Alternatively, the library can be contacted with a target in solution and the target subsequently immobilized. In some embodiments, the target can be brought out of solution by contacting with the solid phase in a process known as panning (Parmley & Smith, *Gene*, 73, 305-318 (1988)). Unbound library members are washed away from the solid phase.

After removal of unbound library members, bound library members can be dissociated from the target and solid phase by, for example, a change in ionic strength or pH, or addition of a substance that competes with the tag for binding to the receptor. For example, binding of metal chelate ligands immobilized on agarose and containing $Ni^{2+}$ to a hexahistidine sequence can be reversed by adding imidazole to the solution to compete for binding of the metal chelate ligand. In some embodiments, antibody-peptide binding can be dissociated by raising the pH to 10.5 or higher.

In some embodiments, the average number of polypeptides per library member selected by this method can be affected by a number of factors. In some cases, decreasing the concentration of target during solution-phase binding can have the effect of increasing the average number of polypeptides in selected library members. In some cases, an increase in the stringency of the washing conditions can also increase the average number of polypeptides per selected library member. In some embodiments, the physical relationship between library members and the solid phase can also be manipulated to increase the average number of polypeptides per library member. For example, if discrete particles are used as the solid phase, decreasing the size of the particles can increase the steric constraints of binding and can require a higher density of polypeptides displayed per library member.

In some embodiments, library members can be amplified before performing a subsequent round of screening, e.g., using techniques such as those described herein. In some embodiments, bound library members can be amplified without dissociating them from the support. For example, gene VIII phage library members immobilized to beads, can be amplified by immersing the beads in a culture of E. coli. Likewise, bacterial display libraries can be amplified by adding growth media to bound library members. Alternatively, bound library members can be dissociated from the solid phase (e.g., by change of ionic strength or pH) before performing subsequent selection, amplification or propagation.

After affinity selection, bound library members can now be enriched for display of polypeptides having specific affinity for the target of interest. In some embodiments, further cycles of affinity enrichment to the screening target can be performed until a desired degree of enrichment has been performed.

In one variation, affinity screening to a target can be performed in competition with a compound that resembles but is not identical to the target. In some embodiments, such screening can preferentially select for library members that bind to a target epitope not present on the compound. In a further variation, bound library members can be dissociated from the solid phase in competition with a compound having known crossreactivity with a target for an antigen. In some cases, library members having the same or similar binding specificity as the known compound relative to the target can be preferentially eluted. In some instances, library members with affinity for the target through an epitope distinct from that recognized by the compound can remain bound to the solid phase.

In some embodiments, libraries produced by the above methods can be characterized by a high proportion of members encoding polypeptides having specific affinity for the target. For example, in some cases, at least 10%, at least 25, at least 50%, at least 75%, at least 95%, or at least 99% of members encode polypeptides having specific affinity for the target. In some embodiments, the exact percentage of members having affinity for the target can depend on whether the library has been amplified following selection, since, in some cases, amplification can increase the representation of genetic deletions. However, in some embodiments, among members with full-length polypeptide coding sequences, the proportion encoding polypeptides with specific affinity for the target can be very high (e.g., at least 50%, at least 75%, at least 95%, or at least 99%). In some embodiments, not all of the library members that encode a polypeptide with specific affinity for the target necessarily can display the polypeptide. For example, in a library in which at least 95% of members with full-length coding sequences encode polypeptides with specific affinity for the target, fewer than half can actually display the polypeptide. Such libraries have, in some embodiments, at least 4, at least 10, at least 20, at least 50, at least 100, at least 1000, at least 10000, or at least 100,000 different coding sequences. In some embodiments, the representation of any one such coding sequences can be no more than 50%, no more than 25%, or no more than 10% of the total coding sequences in the library.

In some embodiments, nucleic acid sequences encoding displayed polypeptides can be subcloned directly into an expression vector without clonal isolation and testing of individual members. In some embodiments, the sequence encoding the outer surface protein of the display vector fused to displayed polypeptides is not excised or amplified in this process. In some cases, the nucleic acids can be excised by restriction digestion of flanking sequences or can be amplified by PCR using primers to sites flanking the coding sequences. See generally *PCR Technology: Principles and Applications for DNA Amplification* (ed. H. A. Erlich, Freeman Press, New York, N.Y., 1992); *PCR Protocols: A Guide to Methods and Applications* (eds. Innis, et al., Academic Press, San Diego, Calif., 1990); Mattila, et al., *Nucleic Acids Res.*, 19:4967 (1991); Eckert, et al., *PCR Methods and Applications*, 1:17 (1991); or PCR (eds. McPherson et al., IRL Press, Oxford). PCR primers can contain a marker sequence that allows positive selection of amplified fragments when introduced into an expression vector. PCR primers can also contain restriction sites to allow cloning into an expression vector, although this is not necessary. In some embodiments, for Fab libraries, if heavy and light chains are inserted adjacent or proximate to each other in a display vector, the two chains can be amplified or excised together. For some Fab libraries, only the variable domains of antibody chain(s) can be excised or amplified. In some embodiments, if the heavy or light chains of a Fab library are excised or amplified separately, they can subsequently be inserted into the same or different expression vectors.

Having excised or amplified fragments encoding displayed polypeptides, the fragments can be size-purified on an agarose gel or sucrose gradient. In some cases, the fragments can run as a single sharp full-length band with a smear at lower molecular corresponding to various deleted forms of coding sequence. The band corresponding to full-length coding sequences can be removed from the gel or gradient and these sequences can be used in subsequent steps.

In some embodiments, the next step is to join the nucleic acids encoding full-length coding sequences to an expression vector thereby creating a population of modified forms of the expression vector bearing different inserts. In some cases, this can be done by conventional ligation of cleaved expression vector with inserts cleaved to have compatible ends. Alternatively, the use of restriction enzymes on insert DNA can be avoided. This method of cloning can be beneficial, in some cases, because naturally encoded restriction enzyme sites can be present within insert sequences, thus, causing destruction of this sequence when treated with a restriction enzyme. For cloning without restricting, the insert and linearized vector sequences are treated briefly with a 3' to 5' exonuclease such as T4 DNA polymerase or exonuclease III (See Sambrook, et al., *Molecular Cloning, A Laboratory Manual* (2nd Ed., CSHP, New York 1989)). The protruding 5' termini of the insert generated by digestion can be complementary to single-stranded overhangs generated by digestion of the vector. The overhangs can be annealed and the reannealed vector transfected into recipient host cells. In some cases, the same result can be accomplished using a 5' to 3' exonuclease rather than a 3' to 5' exonuclease.

In some embodiments, ligation of inserts to expression vector can be performed under conditions that allow selection against reannealed vector and uncut vector. A number of vectors containing conditional lethal genes that allow selection against reannealed vector under nonpermissive conditions are known. See, e.g., Conley & Saunders, *Mol. Gen. Genet.,* 194, 211-218 (1984). In some cases, these vectors effectively allow positive selection for vectors having received inserts. In some instances, selection can also be accomplished by cleaving an expression vector in such a way that a portion of a positive selection marker (e.g., antibiotic resistance) is deleted. In some embodiments, the missing portion can then be supplied by full-length inserts. The portion can be introduced, for example, at the 3' end of polypeptide coding sequences in the display vector or by including in a primer used for amplification of the insert.

In some embodiments, the choice of expression vector depends on the intended host cells in which the vector is to be expressed. For example, the vector can include a promoter and other regulatory sequences in operable linkage to the inserted coding sequences that ensure the expression of the latter. Use of an inducible promoter can be advantageous, in some embodiments, to prevent expression of inserted sequences except under inducing conditions. Non-limiting examples of inducible promoters include arabinose, lacZ, metallothionein promoter, and a heat shock promoter. In some embodiments, cultures of transformed organisms can be expanded under noninducing conditions without biasing the population for coding sequences whose expression products can be better tolerated by the host cells. In some cases, the vector can also provide a secretion signal sequence position to form a fusion protein with polypeptides encoded by inserted sequences. In some embodiments, inserted polypeptides can be linked to a signal sequence before inclusion in the vector. In some cases, vectors that can be used to receive sequences encoding antibody light and heavy chain variable domains can encode constant regions or parts thereof that can be expressed as fusion proteins with inserted chains thereby leading to production of intact antibodies or fragments thereof.

In some embodiments, *E. coli* can be used as the host for cloning the polynucleotides of the present invention. Other non-limiting examples of microbial hosts suitable for use include bacilli, such as *Bacillus subtilis,* and other enterobacteriaceae, such as *Salmonella, Serratia,* and various *Pseudomoras* species. In these prokaryotic hosts, one can also make expression vectors, which can contain expression control sequences compatible with the host cell (e.g., an origin of replication). In addition, any number of a variety of well-known non-limiting promoters can be present, such as the lactose promoter system, a tryptophan (trp) promoter system, a beta-lactamase promoter system, or a promoter system from phage lambda. The promoters typically control expression, optionally with an operator sequence, and can have ribosome binding site sequences and the like, for initiating and completing transcription and translation.

In some embodiments, other microbes, such as yeast, are also be used for expression. For'example, yeast of the genus *Saccharomyces* can be used as a host. In some embodiments, a yeast vector can include an expression control sequence, such as promoters, an origin of replication, termination sequences, and the like.

In some cases, mammalian tissue cell culture can also be used to express and produce the polypeptides (see Winnacker, *From Genes to Clones* (VCH Publishers, New York, N.Y., 1987). A number of suitable host cell lines capable of secreting intact immunoglobulins have been developed including the CHO cell lines, various Cos cell lines, HeLa cells, myeloma cell lines, transformed B-cells and hybridomas. Expression vectors for these cells can include, for example, expression control sequences, such as an origin of replication, a promoter, and an enhancer (Queen, et al., *Immunol. Rev.,* 89:49-68 (1986)), and necessary processing information sites, such as ribosome binding sites, RNA splice sites, polyadenylation sites, and/or transcriptional terminator sequences. Examples of expression control sequences include promoters derived from immunoglobulin genes, SV40, adenovirus, bovine papilloma virus, or cytomegalovirus.

Methods for introducing vectors containing the polynucleotide sequences of interest vary depending on the type of cellular host. For example, calcium chloride transfection is commonly utilized for prokaryotic cells, whereas calcium phosphate treatment or electroporation can be used for other cellular hosts. (See generally Sambrooke, et al., supra). In some embodiments, electroporation can be used. In other embodiments, a transfection reagent such as Lipofectamine™, Lipofectamine 2000™, and others known to those of ordinary skill in the art can be used.

Once expressed, collections of antibodies or other polypeptides can be purified from culture media and/or host cells. In some embodiments, polypeptides can be expressed with signal sequences and released to the culture media. However, if the polypeptides are not naturally secreted by host cells, the polypeptides can be released, for example, by lysis such as by treating with mild detergent. Polypeptides can then be purified by conventional methods including, but not limited to, ammonium sulfate precipitation, affinity chromatography to immobilized target, column chromatography, gel electrophoresis, and the like (see generally Scopes, *Protein Purification* (Springer-Verlag, New York, 1982)).

In some embodiments, the above methods result in novel libraries of nucleic acid sequences encoding polypeptides having specific affinity for a chosen target. The libraries of nucleic acids typically have at least 5, 10, 20, 50, 100, 1000, 10,000 or 100,000 different members. In some embodiments, no single member constitutes more than 25 or 50% of the total sequences in the library. In some embodiments, at least 75%, at least 90%, at least 95%, at least 99%, or at least 99.9% of library members encode polypeptides with specific affinity for the target molecules. In some instances, the nucleic acid libraries can exist in free form, as components of any vector or transfected as a component of a vector into host cells.

In some embodiments, the nucleic acid libraries can be expressed to generate polyclonal libraries of antibodies or other polypeptides having specific affinity for a target. In some cases, the composition of such libraries can be determined from the composition of the nucleotide libraries. In some embodiments, such libraries can have at least 5, 10, 20, 50, 100, 1000, 1,0000 or 100,000 members with different amino acid composition. In some embodiments, no single member can constitute more than 25 or 50% of the total polypeptides in the library. In some libraries, at least 75%, at least 90%, at least 95%, at least 99%, or at least 99.9% of polypeptides have specific affinity for the target molecules. The different polypeptides can differ from each other in terms of fine binding specificity and affinity for the target.

In some embodiments, preparations of antibodies and other polypeptides can be incorporated into compositions for diagnostic or therapeutic use. The composition used can depend on the intended mode of administration and diagnostic or therapeutic application. In some cases, the compositions can also include, depending on the formulation desired, pharmaceutically-acceptable, non-toxic carriers or diluents, which are defined as vehicles commonly used to formulate pharmaceutical compositions for animal or human administration. The diluent can be selected so as not to affect the biological activity of the combination. Non-limiting examples of such diluents include distilled water, physiological phosphate-buffered saline, Ringer's solutions, dextrose solution, and Hank's solution. In addition, the pharmaceutical composition or formulation can also include other carriers, adjuvants, or nontoxic, nontherapeutic, non-immunogenic stabilizers, and the like. See *Remington's Pharmaceutical Science*, (15th ed., Mack Publishing Company, Easton, Pa., 1980). Generally, compositions intended for in vivo use can be sterile.

Kits

In one embodiment, a kit can be provided, containing one or more of the above compositions. A "kit," as used herein, typically defines a package or an assembly including one or more of the compositions of the invention, and/or other compositions associated with the invention, for example, as previously described. Each of the compositions of the kit can be provided in liquid form (e.g., in solution), in solid form (e.g., a dried powder), etc. A kit of the invention can, in some cases, include instructions in any form that are provided in connection with the compositions of the invention in such a manner that one of ordinary skill in the art would recognize that the instructions are to be associated with the compositions of the invention. For instance, the instructions can include instructions for the use, modification, mixing, diluting, preserving, administering, assembly, storage, packaging, and/or preparation of the compositions and/or other compositions associated with the kit. The instructions can be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

Kits for producing an amplified library of clones are also described herein. Such kit includes (a) a container comprising a library of clones, the library of clones comprising a plurality of distinguishable replicable genetic package members; and (b) at least one microfluidic device for generating monodisperse droplets. Examples of replicable genetic package include, but are not limited to, a virus, a eukaryotic cell, a spore, a yeast cell, a bacterial cell, a nucleic acid sequence, or a recombinant thereof. Accordingly, the library of clones can be a phage display library, a yeast display library, a ribosome display library, a cell surface display library, a DNA display library, a RNA display library, a bacterial display library, or a commercially-available library (e.g., New England BioLabs: Ph.D.™ Peptide Display Cloning System; Ph.D.™-12 Phage Display Peptide Library; Ph.D.™-7 Phage Display Peptide Library; Ph.D.™-C7C Phage Display Peptide Library; or Invitrogen: Yeast Display Library or *E. Coli* Display Library).

When the replicable genetic package is a virus (e.g., a phage), the kit can further comprise a container comprising at least one host cell (e.g., a plurality of host cells such as bacterial cells) capable of supporting replication of the replicable genetic package.

Accordingly, kits for producing an amplified library of phage clones are also provided herein. The kit for phage amplification includes (a) a container comprising a library of phage clones; (b) a container comprising a plurality of bacterial cells (e.g., *E. Coli*, or F+ bacteria); and (c) at least one microfluidic device for generating monodisperse droplets.

In some embodiments, any kit described herein can further comprise one or more containers comprising at least one surfactant described herein. In some embodiments, any kit described herein can further comprise one or more containers comprising at least one perfluorinated liquid. In some embodiments, any kit described herein can further comprise one or more containers comprising at least one destabilization agent. In some embodiments, any kit described herein can further comprise one or more containers comprising growth or replication media (e.g., LB media for bacteria or cell culture medium specific for each individual cell types, or nucleotides and polymerase for nucleic acid amplification). In some embodiments, any kit described herein can further comprise at least one syringe, at least one tubing or a combination thereof. In some embodiments, any kit described herein can further comprise at least one container for collecting droplets produced from the at least one microfluidic device. An instruction manual for producing the amplified library can also be provided in some embodiments of any kit described herein.

The present invention may be defined in any of the following numbered paragraphs:

1. A method of producing an amplified library of clones, the method comprising:
   a. distributing a library of clones comprising a plurality of distinguishable replicable genetic package members into a plurality of monodisperse individual compartments such that substantially no more than one replicable genetic package member is contained in any individual compartment; and
   b. amplifying the library of step (a) for a sufficient period of time such that each of the distinguishable members replicates to reach substantially the same copy number within the individual compartments;

thereby maintaining diversity of the library of clones upon amplification.

2. The method of paragraph 1, wherein the replicable genetic package is a virus, a eukaryotic cell, a spore, a yeast cell, a bacterial cell, a nucleic acid sequence, or a recombinant thereof.

3. The method of paragraph 1 or 2, wherein the replicable genetic package is a virus, and wherein substantially each of the individual compartments further comprises at least one host cell capable of supporting replication of the replicable genetic package, wherein the number of host cells within each of the individual compartments is substantially the same.

4. The method of paragraph 3, wherein substantially each of the individual compartments further comprises at least ten host cells capable of supporting replication of the replicable genetic package.

5. The method of paragraph 3 or 4, wherein the virus is a bacteriophage and the host cells are bacterial cells.

6. The method of any of paragraphs 1-5, wherein each of the individual compartments further comprises growth or replication media containing substantially the same amounts of nutrients.

7. The method of any of paragraphs 1-6, wherein each of the distinguishable members replicates to reach saturation.

8. The method of paragraph 7, wherein the saturation is reaching a maximum copy number allowed in the individual compartments.

9. The method of any of paragraphs 1-8, wherein the individual compartments are fluidic droplets.

10. The method of any of paragraphs 1-9, wherein the plurality of distinguishable replicable genetic package members are distributed into a plurality of fluidic droplets using at least one microfluidic device.

11. The method of paragraph 9 or 10, wherein the fluidic droplets are suspended in a perfluorinated liquid and stabilized by at least one surfactant.

12. The method of any of paragraphs 1-11, further comprising the step of releasing the amplified distinguishable members within the individual compartments into one common fluid.

13. The method of paragraph 12, wherein the step of releasing is performed by adding at least one destabilization agent into the amplified library of step (b).

14. The method of paragraph 12 or 13, wherein the step of releasing is performed by diluting the at least one surfactant.

15. The method of any of paragraphs 12-14, wherein the step of releasing is performed in the presence of electric fields.

16. The method of any of paragraphs 1-15, wherein the monodisperse compartments have an average diameter of at least about 40 µm.

17. The method of any of paragraphs 1-16, wherein the monodisperse compartments have an average diameter of about 20 µm to about 500 µm.

18. The method of any of paragraphs 1-17, wherein the monodisperse compartments have an average diameter of no larger than 200 µm.

19. The method of any of paragraphs 1-18, wherein the library comprises at least about 100 distinguishable clones.

20. The method of any of paragraphs 1-19, wherein the library comprises at least about 1,000 distinguishable clones.

21. The method of any of paragraphs 1-20, wherein the library comprises at least about $10^6$ distinguishable clones.

22. The method of any of paragraphs 1-21, wherein the library comprises at least about $10^9$ distinguishable clones.

23. The method of any of paragraphs 1-22, wherein the amplified library of clones is selected from the group consisting of phage display, yeast display, bacterial display, RNA display, DNA display, and ribosome display.

24. A method of producing an amplified library of phage clones, the method comprising:
   a. distributing a library of phage clones comprising a plurality of distinguishable phage clones into a plurality of monodisperse individual compartments such that substantially no more than one phage clone is contained in any individual compartment, and wherein each of the individual compartments further comprises at least one bacterial cell; and
   b. culturing the library of step (a) for a sufficient period of time such that the bacterial cells replicate essentially to the same number within the individual compartments, thereby producing substantially the same copy number of each phage clone within the individual compartments;
   thereby maintaining diversity of the library of phage clones upon amplification.

25. The method of paragraph 24, wherein substantially each of the individual compartments further comprises at least ten bacterial cells.

26. The method of any of paragraphs 24-25, wherein each of the individual compartments further comprises growth or replication media containing substantially the same amounts of nutrients.

27. The method of any of paragraphs 24-26, wherein the bacterial cells within the individual compartments replicate to reach growth saturation.

28. The method of paragraph 27, wherein the growth saturation is reaching maximum density of growth.

29. The method of any of paragraphs 24-28, wherein the individual compartments are fluidic droplets.

30. The method of any of paragraphs 24-29, wherein substantially no more than one distinguishable phage clone is distributed into any individual fluidic droplets using at least one microfluidic device.

31. The method of paragraph 29 or 30, wherein the fluidic droplets are suspended in a perfluorinated liquid and stabilized by at least one surfactant.

32. The method of any of paragraphs 24-31, further comprising the step of releasing the amplified distinguishable clones within the individual compartments into one common fluid.

33. The method of paragraph 32, wherein the step of releasing is performed by adding at least one destabilization agent into the culture of step (b).

34. The method of paragraph 32 or 33, wherein the step of releasing is performed by diluting the at least one surfactant.

35. The method of any of paragraphs 32-34, wherein the step of releasing is performed in the presence of electric fields.

36. The method of any of paragraphs 24-35, wherein the monodisperse compartments have a size of at least about 40 µm.

37. The method of any of paragraphs 24-36, wherein the monodisperse compartments have a size of about 20 µm to about 500 µm.

38. The method of any of paragraphs 24-37, wherein the monodisperse compartments have a size of no larger than 200 µm.

39. The method of any of paragraphs 24-38, wherein the library comprises at least about 100 distinguishable clones.

40. The method of any of paragraphs 24-39, wherein the library comprises at least about 1,000 distinguishable clones.

41. The method of any of paragraphs 24-40, wherein the library comprises at least about $10^6$ distinguishable clones.

42. The method of any of paragraphs 24-41, wherein the library comprises at least about $10^9$ distinguishable clones.

43. A library of phage clones produced by the method of any of paragraphs 24-42, wherein the copy number of each phage clone is substantially the same.

44. A kit for producing an amplified library of clones comprising:
   a. a container comprising a library of clones, the library of clones comprising a plurality of distinguishable replicable genetic package members; and
   b. at least one microfluidic device for generating monodisperse droplets.

45. The kit of paragraph 44, wherein the replicable genetic package is a virus, a eukaryotic cell, a spore, a yeast cell, a bacterial cell, a nucleic acid sequence, or a recombinant thereof.

46. The kit of paragraph 44 or 45, further comprising at least one host cell capable of supporting replication of the replicable genetic package when the replicable genetic package is a virus.
47. The kit of any of paragraphs 44-46, further comprising one or more containers comprising at least one surfactant.
48. The kit of any of paragraphs 44-47, further comprising one or more containers comprising at least one perfluorinated liquid.
49. The kit of any of paragraphs 44-48, further comprising one or more containers comprising at least one destabilization agent.
50. The kit of any of paragraphs 44-49, further comprising one or more containers comprising growth or replication media.
51. The kit of any of paragraphs 44-50, further comprising at least one syringe, at least one tubing or a combination thereof.
52. The kit of any of paragraphs 44-51, further comprising at least one container for collecting droplets produced from the at least one microfluidic device.
53. The kit of any of paragraphs 44-52, further comprising an instruction manual for producing the amplified library.
54. A kit for producing an amplified library of phage clones comprising:
   a. a container comprising a library of phage clones;
   b. a container comprising a plurality of bacterial cells; and
   c. at least one microfluidic device for generating monodisperse droplets.
55. The kit of paragraph 54, further comprising one or more containers comprising at least one surfactant.
56. The kit of any of paragraphs 54-55, further comprising one or more containers comprising at least one perfluorinated liquid.
57. The kit of any of paragraphs 54-56, further comprising one or more containers comprising at least one destabilization agent.
58. The kit of any of paragraphs 54-57, further comprising one or more containers comprising growth or replication media.
59. The kit of any of paragraphs 54-58, further comprising at least one syringe, at least one tubing or a combination thereof.
60. The kit of any of paragraphs 54-59, further comprising at least one container for collecting droplets produced from the at least one microfluidic device.
61. The kit of any of paragraphs 54-60, further comprising an instruction manual for producing the amplified library.
62. A method of producing an amplified library of viral clones, the method comprising:
   providing an initial library of replicable genetic packages having a first distribution of growth rates including a first mean and a first standard deviation; and
   amplifying the initial library of replicable genetic packages to produce an amplified library of replicable genetic packages having a second distribution of growth rates including a second mean and a second standard deviation, wherein the first mean and the second mean differ by no more than about 10% relative to the first mean and the first standard deviation and the second standard deviation differ by no more than about 10% relative to the first standard deviation.
63. The method of paragraph 62, wherein essentially each of the replicable genetic packages are contained in individual compartments such that the replicable genetic packages are isolated from each other.
64. The method of any one of paragraphs 62 or 63, wherein the act of amplifying the initial library of replicable genetic packages comprises providing a plurality of fluidic droplets, containing members of the initial library such that essentially each member is contained in an individual fluidic droplet, and amplifying essentially each member of the initial library.
65. The method of any one of paragraphs 62-64, wherein the average diameters of the fluidic droplets are less than 1 mm.
66. The method of any one of paragraphs 62-65, wherein the fluidic droplets are contained within a microfluidic channels.
67. The method of any one of paragraphs 62-66, wherein essentially each replicable genetic package in the initial library of replicable genetic packages is isolated from the other replicable genetic packages.
68. The method of paragraph 67, wherein the replicable genetic packages are contained in individual compartments, wherein essentially each of the individual compartments has essentially the same concentration of a nutrient.
69. The method of any one of paragraphs 62-68, wherein the first mean and the second mean differ by no more than about 50% relative to the first mean.
70. The method of any one of paragraphs 62-69, wherein the first mean and the second mean differ by no more than about 20% relative to the first mean.
71. The method of any one of paragraphs 62-70, wherein the first standard deviation and the second standard deviation differ by no more than about 50% relative to the first standard deviation.
72. The method of any one of paragraphs 62-71, wherein the first standard deviation and the second standard deviation differ by no more than about 20% relative to the first standard deviation.
73. The method of any one of paragraphs 62-72, wherein the replicable genetic packages of the initial library are bacteriophages.
74. The method of any one of paragraphs 62-73, wherein the replicable genetic packages of the initial library are bacteria.
75. The method of any one of paragraphs 62-74, wherein the replicable genetic packages of the initial library are eukaryotic cells.
76. An article, comprising:
   a viral library comprising a plurality of distinguishable clones, essentially each distinguishable clone contained within discrete microfluidic droplets, wherein the microfluidic droplets have a distribution of volumes such that at least about 90% of the droplets have a volume that varies by no more than about 10% relative to the average volume of the droplets.
77. The article of paragraph 76, wherein the clones of the plurality of distinguishable clones are essentially each contained in individual compartments.
78. The article of any one of paragraphs 76 or 77, wherein the microfluidic droplets further contain cells.
79. The article of any one of paragraphs 76-78, wherein the microfluidic droplets essentially each contain essentially the same concentration of a nutrient.
80. The article of any one of paragraphs 76-79, wherein the viral library comprises at least about 100 distinguishable clones.
81. The article of any one of paragraphs 76-80, wherein the viral library comprises at least about 1,000 distinguishable clones.

82. The article of any one of paragraphs 76-81, wherein the viral library comprises at least about 106 distinguishable clones.

83. The article of any one of paragraphs 76-82, wherein the viral library comprises at least about 109 distinguishable clones.

84. A method of producing an amplified library of viral clones, the method comprising:
providing a first compartment having a first volume and a second compartment having a second volume, the first compartment containing a first viral clone and the second compartment containing a second viral clone, wherein the first viral clone growth rate and the second viral clone growth rate differ by at least about 10% relative to the slower growth rate of the first and second viral clones; and
amplifying the first viral clone and the second viral clone such that the ratio of the number of first viral clone particles to the number of second viral clone particles after amplification is essentially equal to the volumetric ratio of the first volume to the second volume.

85. The method of paragraph 84, further comprising amplifying the first viral clone and the second viral clone by at least 10-fold.

86. The method of any one of paragraphs 84 or 85, wherein the first compartment and the second compartment each contain a cell.

87. The method of any one of paragraphs 84-86, wherein the first compartment is a first fluidic droplet, and the second compartment is a second fluidic droplet.

88. The method of paragraph 87, wherein the first fluidic droplet and the second fluidic droplet are each contained within a microfluidic channel.

89. The method of any one of paragraphs 87 or 88, wherein the first fluidic droplet has an average diameter of less than 1 mm, and the second fluidic droplet has an average diameter of less than 1 mm.

90. An article, comprising:
a phage display library comprising at least 10,000 distinguishable viral clones having varying growth rates, wherein the highest growth rate of the viral clones is at least 10 times greater than the slowest growth rate of the viral clones, and wherein essentially each of the distinguishable viral clones contains at least 10,000 copies.

Some Selected Definitions

As used herein, the term "host cell" includes an individual cell or cell culture which can be or has been a recipient or a carrier of at least one replicable genetic package, e.g., viruses, and nucleic acid sequences. Host cells include progeny of a single host cell, and the progeny may not necessarily be completely identical (in morphology or in total DNA complement) to the original parent cell due to natural, accidental, or deliberate mutation and/or change. In some embodiments, a host cell can include cells transfected or infected in vitro with at least one replicable genetic package, e.g., viruses, and nucleic acid sequences. In some embodiments, a host cell includes cells that can be or will be transfected or infected in vitro with at least one replicable genetic package, e.g., viruses, and nucleic acid sequences. In various embodiments, a host cell can be a prokaryotic cell. In other embodiments, a host cell can be a eukaryotic cell.

As used herein, the term "substantially" or "essentially" means a proportion of at least about 60%, or preferably at least about 70% or at least about 80%, or at least about 90%, at least about 95%, at least about 97% or at least about 99% or more, or any integer between 70% and 100%. In some embodiments, the term "substantially" means a proportion of at least about 90%, at least about 95%, at least about 98%, at least about 99% or more, or any integer between 90% and 100%. In some embodiments, the term "substantially" can include 100%.

Other than in the operating examples, or where otherwise indicated, all numbers expressing quantities of ingredients or reaction conditions used herein should be understood as modified in all instances by the term "about." The term "about" when used in connection with percentages may mean±1%.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified throughout the specification are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The following examples are intended to illustrate certain embodiments of the present invention, but do not exemplify the full scope of the invention.

The contents of all references cited throughout this application, examples, as well as the figures and tables are incorporated herein by reference in their entirety.

Example 1

This prophetic example demonstrates dynamics of growth of a mixture of rapidly amplifying and slowly amplifying phage in the same solution.

In this example, phage A and phage B are provided, where phage B has an infection rate 25% lower than that of phage A. When the two phage are mixed with $10^9$ bacteria, phage A goes through four cycles of infection and secretion ($1$-->$10^3$-->$10^6$-->$10^9$-->$10^{12}$), whereas phage B goes through only three cycles in the same period of time. The resulting population of phage B in the amplified mixture will be 1,000 times less than that of phage A. Exponential amplification, and the large number of clones secreted at each cycle, can make the amplification process sensitive even to subtle differences in growth rate.

Example 2

This prophetic example demonstrates how to calculate the concentration of phage in droplets of different sizes, in accordance with one embodiment of the invention.

When a solution of volume V containing N phage is broken into M monodisperse droplets, the probability of finding at least one phage in a droplet can be given by Poisson statistics: the average number of infected droplets $M_{inf}$ is given by Equation 1:

$$M_{inf} = M(1 - e^{-\frac{N}{M}}) \quad (1)$$

In this example, in every infected droplet, phage can be amplified to a plateau concentration of $10^{12}$ pfu/mL. Because the droplets are monodisperse, the volume of each droplet is V/M, and the number of phage in an infected droplet is $10^{12}$V/M. After combining all droplets in one solution, the final number of phage $N_f$ in this solution is a product of $M_{inf}$ and the number of phage per droplet (Equation 2):

$$N_f = 10^{12} V(1 - e^{-\frac{N}{M}}) \quad (2)$$

Equation 2 can be rewritten by expressing the number of phage N using the concentration of phage (C=N/V), and the number of droplets M using the volume of a droplet $V_d$ (M=V/$V_d$) to yield Equation 3:

$$N_f = 10^{12} V(1 - e^{-CV_d}) \quad (3)$$

For constant V and C, the final concentration of phage decreases with the droplet size.

In the above derivation, it was assumed that in each droplet the phage grow to a concentration of $10^{12}$ pfu/mL. This assumption is true if: (a) each droplet contains at least one bacterium, i.e., the probability of finding a droplet that has phage but no bacteria is less than 1/M (Equation 4, where $N_b$ is the number of bacteria in volume V):

$$e^{-\frac{N_b}{M}}(1 - e^{-\frac{N}{M}}) < \frac{1}{M} \quad (4)$$

and (b) bacteria reach the same saturating concentration in each droplet. Without wishing to be bound by any theory, this assumption in general can not be true because the maximum number of bacteria in droplets is also described by a probability distribution. It is predicted that for very small droplets that can support ~10 bacteria, variations in the number of bacteria can lead, in certain embodiments, to variations in the concentration of phage produced in each droplet.

Example 3

This prophetic example demonstrates encapsulation in droplets for amplification of large libraries of phage.

If a library contains N different phage clones (where every clone is different), how many droplets (M) should be generated to minimize the probability of two different phage clones residing in the same droplet? To answer this question, the number of droplets ($N_{2+}$) containing two of more phages clones ("mixed droplets") can be estimated using a Poisson distribution (Equation 5):

$$N_{2+} = M\left(1 - e^{-\frac{N}{M}}\left(1 + \frac{N}{M}\right)\right) \quad (5)$$

To use this equation, an acceptable number of mixed droplets ($N_{2+}$) should be defined. The total number of drops M, in turn, is found by solving Equation 5 for given values of N and $N_{2+}$.

Example 4

This example demonstrates amplification of phage with different growth characteristics in individual droplets.

To model competition between phage clones, two sets of phage clones were used: (1) a commercially available library of M13 filamentous phage that was engineered to present a 12-mer peptide on the PIII coat protein, and (2) a non-engineered, wild-type ("wt") phage (also known as "environmental phage"). Because wt infects bacteria more effectively than engineered phage, wt provides a model of a "rapidly growing phage" (R) while the engineered library provides a model of a "slowly growing phage" (S).

Figure 1B:
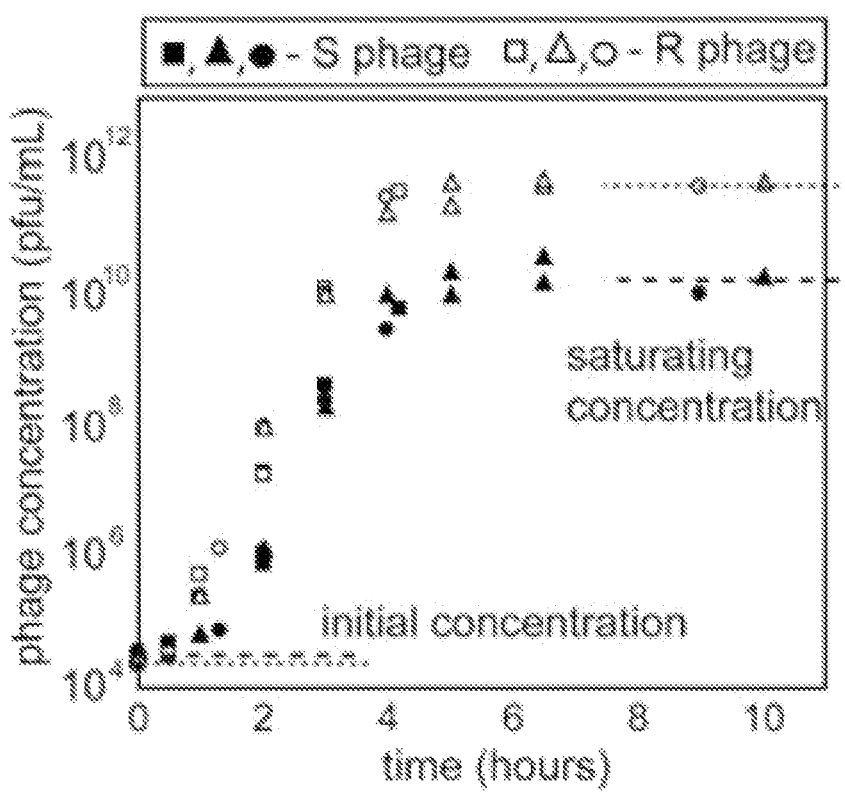
FIG. 1B shows an example graph depicting time dependence of concentration of slow-growing (S) and rapid-growing (R) phage that compete for bacterial hosts in the same solution.
Figure 1C:
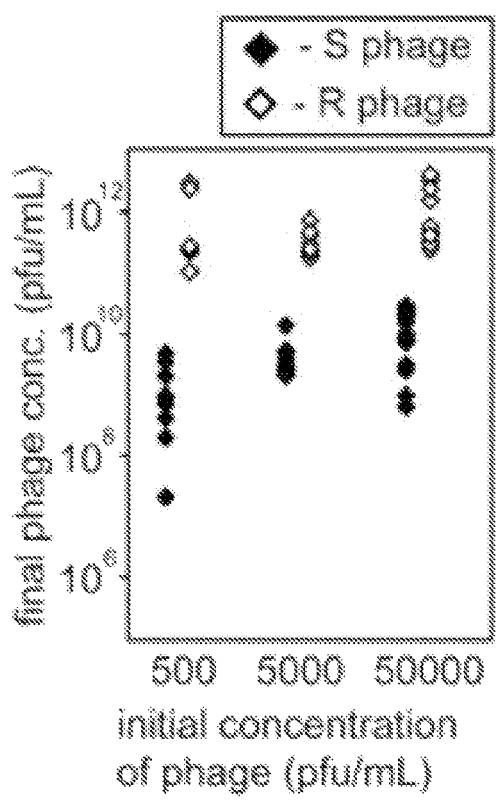
FIG. 1C shows an example graph depicting initial and final phage concentrations.

In this example, S phage contained a galactosidase reporter and formed blue plaques in bacterial colonies on solid media containing the colorimetric galactosidase substrate, X-gal. Reporter-free R phage formed clear plaques under the same conditions, allowing it to be distinguished from S phage. During growth of a mixture of S and R phage in a common suspension of E. coli, the R/S ratio increased exponentially with time. For example, during replication of a mixture of R and S phage that was originally 1:1, the first burst of progeny from the R phage appeared sooner than that for S (FIG. 1B). This figures shows time-dependence of concentration of slow-growing (S) and rapid-growing (R) that compete for the bacteria host in the same solution (results from three independent experiments; all data are presented). Dashed grey and white lines show the average saturating concentration of S and R. This ratio reached 45 in amplification from 50,000 to $10^{11}$ pfu/mL, and 300 in amplification from 500 to $10^{11}$ pfu/mL (FIG. 1C). In this figure, 500+500, 5,000+5,000 or 50,000+50,000 pfu of S and R phage were mixed, bacteria were added, and the concentration of S and R after seven hours of amplification was measured (results from three independent experiments; all data are presented).

Figure 2A:
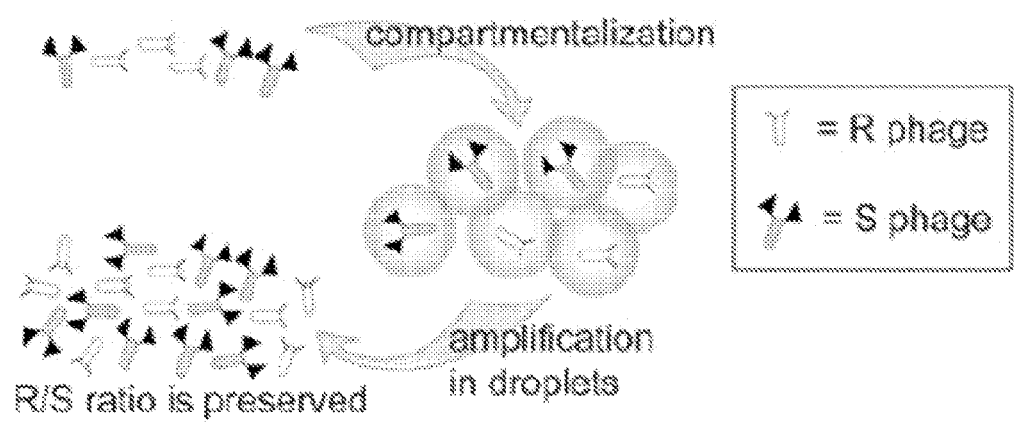
FIG. 2A is a schematic diagram illustrating amplification of two types of phage in separate droplets, according to one or more embodiments of the invention.

In contrast, when R and S phage were amplified in separate solutions, they both reached a limiting concentration of (3-5)×$10^{11}$ pfu/mL, maintaining the original ratio of 1:1. To separate phage clones, the individual phage clones were placed inside droplets of growth media, generated by a microfluidic flow-focusing device (MFFD), suspended in a perfluorinated liquid, and stabilized by a biocompatible fluoro-surfactant (FIGS. 2A and 2B). This combination of carrier fluid and surfactant yielded stable drops that did not coalesce even when they were rocked for 48 hours.

Figure 2C:
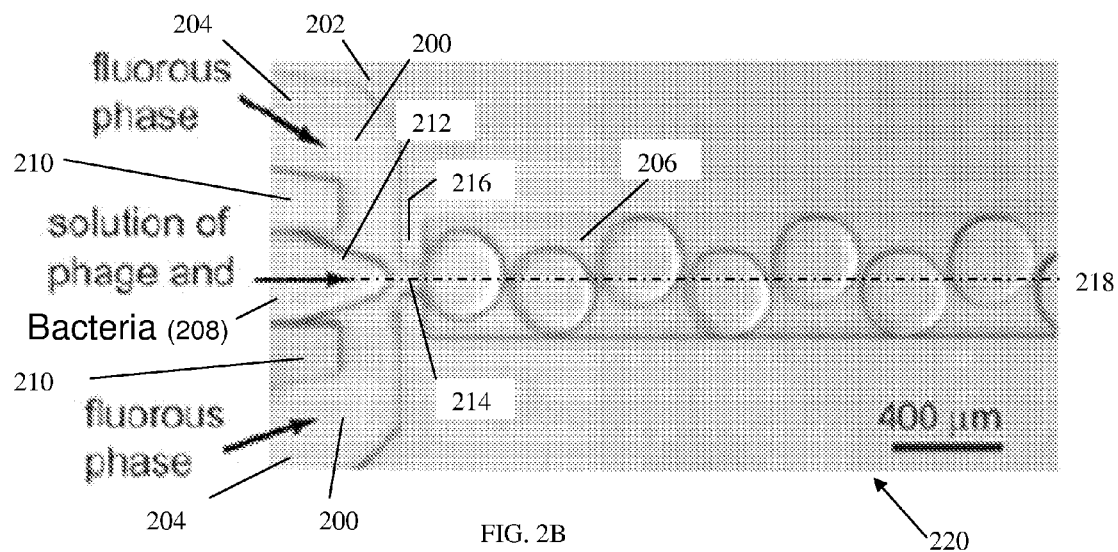
FIGS. 2C-2D show images of bacteria inside droplets, according to one or more embodiments of the inventions, wherein the arrow heads in FIG. 2C indicate bacteria and the arrow in FIG. 2D indicates dividing bacteria.
Figure 2D:
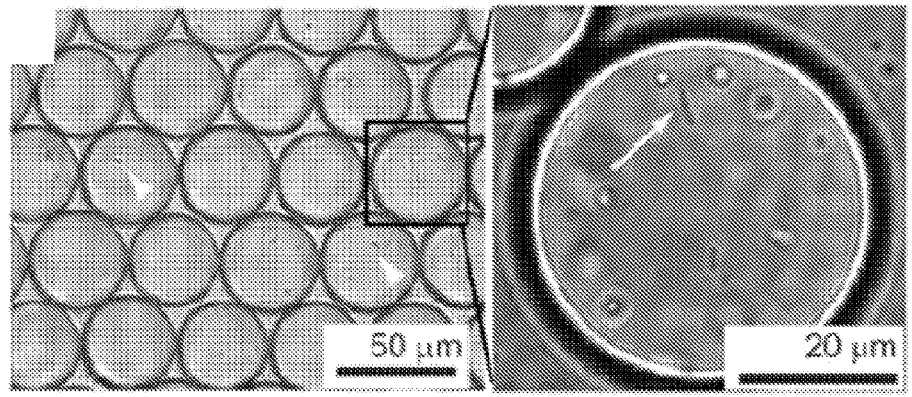
Figure 2E:
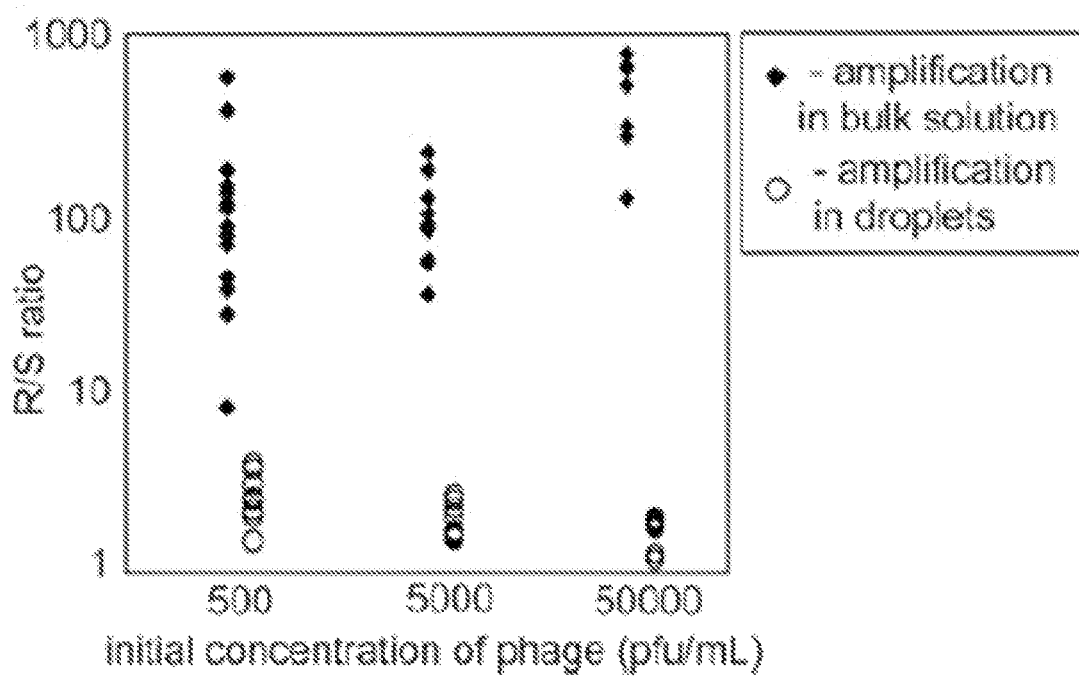
FIG. 2E shows a graph of the ratio of rapidly-growing phage to slowly-growing phage as a function of different initial concentrations of phage, wherein the phages were amplified either in bulk solution or in individual compartments in accordance with certain embodiments.
Figure 2F:
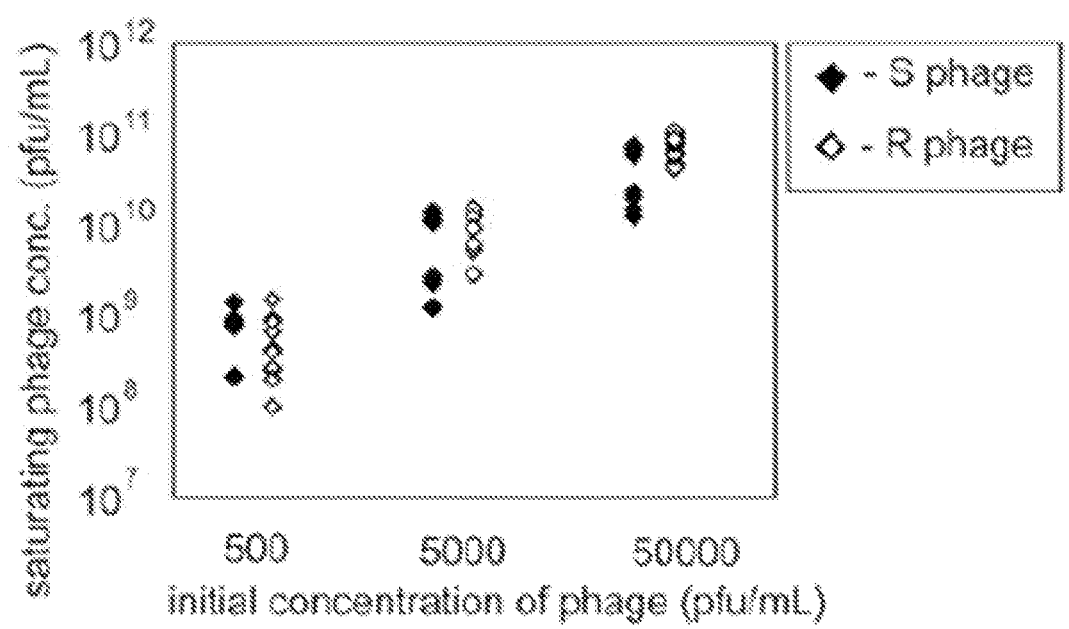
FIG. 2F shows a graph of saturating phage concentration as a function of initial concentration of phage in accordance with some embodiments.

FIGS. 2C-2D show image of bacteria inside droplets (arrow heads), and higher-resolution image showing dividing bacteria in a droplet (arrow). The images were acquired using inverted phase-contrast microscope with 20× and 100× oil-immersion objective R/S ratio obtained by amplification of a 1:1 mixture of R and S phage in bulk solution or in droplets. The number of phage obtained by amplification of phage at initial concentrations of 500, 5,000 or 50,000 pfu/mL, respectively, were compared; graph contains results from two to four independent experiments, with two to four measurements in each experiment. The phage did not hop between droplets (FIG. 2E) and thus, when the initial number of phage was much smaller than the number of droplets, the final concentrations of R and S were proportional to the initial numbers of R and S phage. The data are the results from three independent experiments. The final concentrations of R and S were proportional to the initial numbers of R and S phage (FIG. 2F). FIGS. 2E and 2F present all data (i.e., no selection; 2-5 experiments); the overlaying grey bar is equal to 2× (standard deviation).

The use of the MFFD allowed fine control of drop size as evidenced by narrow polydispersity (1.01). Phage and bacteria were mixed, and droplets were generated from this mixture before the first burst of phage production occurred (within 30-45 min). Operating the MFFD at rates of flow between 2-6 mL/hr, 1-3 mL of compartmentalized phage were generated within 30 min. For droplets of ~200 micrometers in diameter, the rates corresponded to $2\times10^5$-$7\times10^5$ droplets. After compartmentalization, the emulsions were gently rocked at 36° C. to allow for growth of E. coli and production of phage. Seven hours later, the emulsions were destabilized, and the concentration of phage in the medium was estimated using a plaque forming assay. Importantly, bacteria did not cross between the droplets FIGS. 4A and 4B. Hence, bacteria carrying phage plasmids remain confined to one droplet.

Figure 4A:
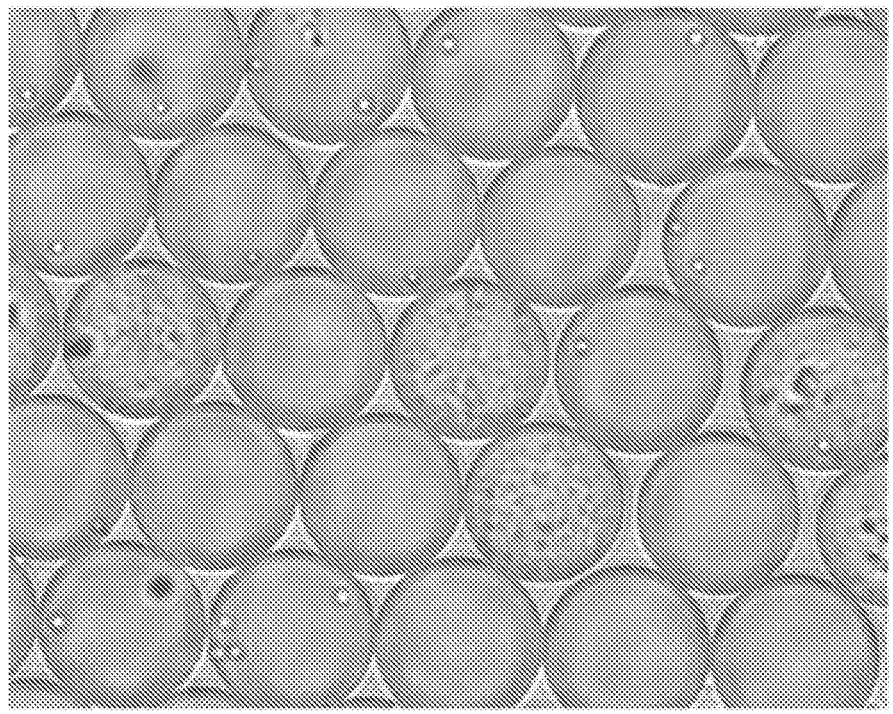
FIG. 4A shows, in accordance with one embodiment, a phase-contrast image of 40-micrometer droplets containing bacteria.
Figure 4B:
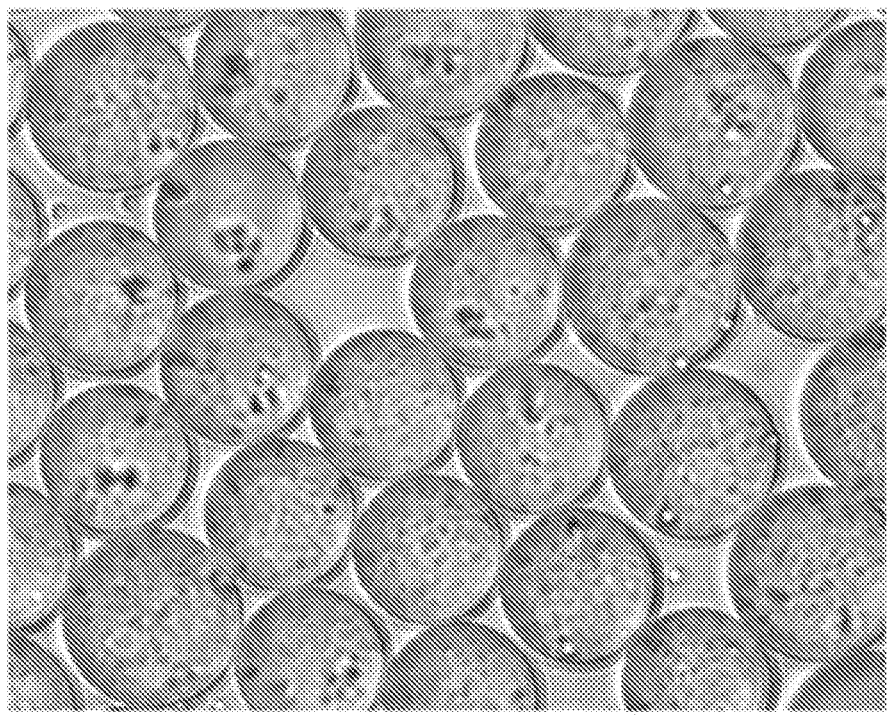
FIG. 4B shows, in accordance with another embodiment, a phase-contrast image of 40-micrometer droplets containing bacteria.

In particular, FIG. 4A shows phase-contrast image of 40-micrometer droplets containing bacteria after eight hours of incubation at 36° C. The droplets were formed from a solution containing $8\times10^6$ cfu/mL. Because ~$3\times10^7$ droplets were formed from 1 mL of the solution, the above concentration of bacteria, statistically, yielded one bacterium in only one-forth of the droplets. Indeed, only less than 30% of the droplets were infected eight hours later. FIG. 4B shows a similar phase-contrast image of 40-micrometer droplets containing bacteria after eight hours of incubation at 36° C. Where the concentration of bacteria was ten times higher ($8\times10^7$ cfu/mL), nearly all drops were infected. The global concentration of bacteria in FIG. 4A and FIG. 4B was compared, and it was observed that FIG. 4B contained three times higher concentrations of bacteria than FIG. 4A. These measurements confirmed that bacteria in each droplet grew to a maximum concentration of ~50-60 cfu/mL, and that bacteria did not contaminate the adjacent droplets. To measure the global concentration, the droplets were extracted, and the concentration of bacteria was measured in the combined aqueous solution using a colony-forming assay (the numbers were an average from eight measurements in two independent samples). The images were acquired using an inverted microscope with 40× objective.

To demonstrate that separation of slow and fast phage in droplets eliminated competition, a 1:1 mixture of S and R phage was used at different total concentrations of phage ($10^5$, $10^4$, $10^3$ pfu/mL) and mixed with $10^8$ cfu/mL of bacteria to generate droplets of $10^{-6}$ mL. Each drop in this set of experiments thus contained, on average, ~100 bacteria and either one phage or no phage. Under these conditions, the probability that S and R phage would be present in the same droplet was small.

These experiments yielded two useful observations: (1) the final R/S ratio of phage amplified in the mixture of droplets remained close to the initial ratio of ~1:1 (FIG. 2E); this ratio was not preserved in amplification of phage in bulk solution, and R/S exceeded 100:1 (FIGS. 2E and 1C), and (2) when amplified in droplets, the final total concentration of phage was proportional to the starting concentration of phage (FIG. 2F). This observation confirmed that phage did not hop between the droplets. If phage were able to cross the fluorous phase and infect bacteria in neighboring droplets, the final concentration of phage in all samples would be expected to reach $(3-5)\times10^{11}$ pfu/mL.

Figure 3A:
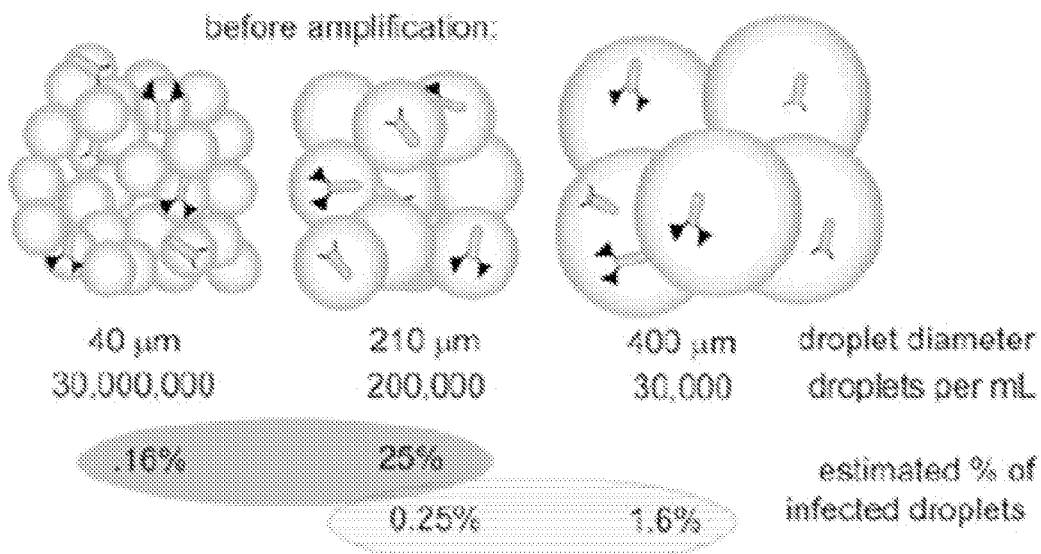
FIG. 3A is a schematic diagram comparing amplification of phage placed in droplets of different sizes, in certain embodiments, wherein estimated % of infected droplets is calculated by dividing initial concentration of phage in PFU/mL by number of droplets per mL.
Figure 3B:
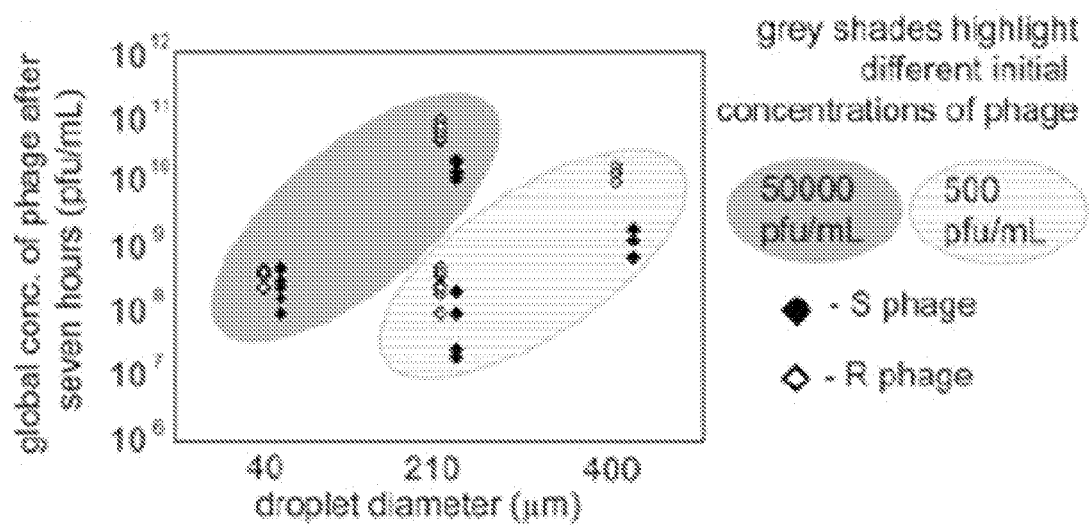
FIG. 3B shows a plot of total concentration of phage amplified from 500 or 50,000 pfu (plaque forming units) per mL of S- and R-phage as a function of droplet size, in particular embodiments.

How the number of phage in drops depended on the drop size was also examined. A suspension of a mixture of R and S phage (and bacteria) was distributed at a fixed concentration into emulsions made of droplets of different sizes (FIGS. 3A and 3B). FIG. 3A shows amplification of 1:1 mixtures of S and R phage of the same concentrations placed in droplets of different sizes were compared. The percentage of infected droplets was estimated as (initial concentration of phage, pfu/mL)/(number of droplets per mL). FIG. 3B shows a plot of total concentration of phage amplified from 500 or 50,000 pfu of S and R phage. For the same initial concentration of phage, increase in droplet size increased the number of compartments occupied by phage (see FIG. 3A) and led to higher concentration of phage after amplification. After amplification, the number of phage per droplet increased in proportion to the volume of the droplet. This relation indicates the importance of monodispersity in droplet size. If different phage clones were isolated from each other in polydisperse emulsions (e.g. those generated by vortexing), distribution of phage amplified in this condition would essentially mirror the polydispersity of the distribution of volumes of drops.

Figure 3C:
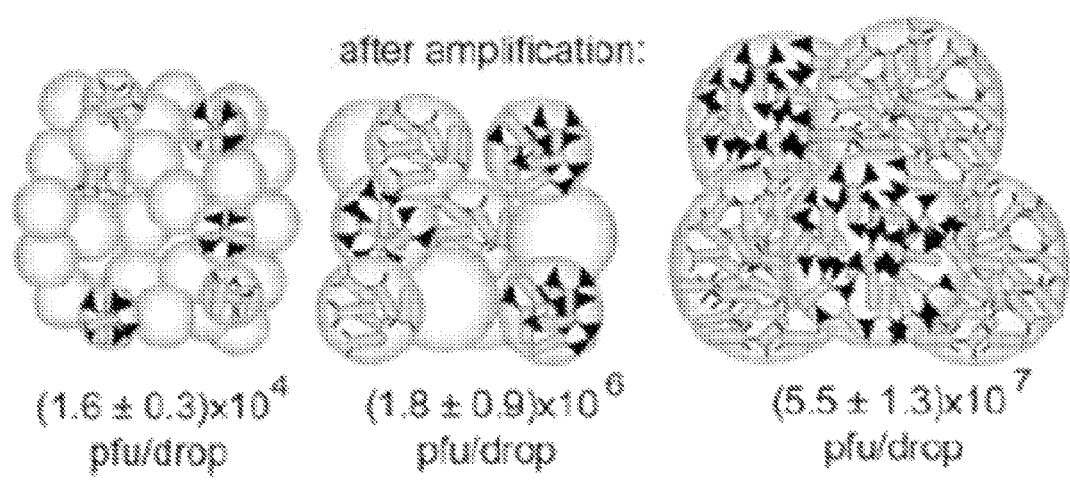
FIG. 3C compares droplets containing a concentration range of amplified phages, according to another embodiment.

Because phage did not hop between droplets, the number of phage per drop after amplification could be estimated as (final concentration of phage, pfu/mL)/(number of infected droplets per mL). Droplets ranging from $5\times10^{-8}$ mL (diameter ~40 um) to $5\times10^{-5}$ mL (diameter ~670 um) are suitable for this approach. It was observed that the droplets of diameter smaller than 40 micrometers could support growth of only a few bacteria and are not practical for amplification of phage. Drops much larger than 500 micrometers were unstable and susceptible to disruption into smaller drops by shear during incubation or rocking. To process more than 2-3 mL of phage solution, parallel droplet generation could be employed. Alternatively, the microfluidic device could be run for at least 30 min if the mixture of bacteria and phage were cooled below room temperature to delay production of new phage. The system used required minimal peripheral equipment (two syringe pumps and a camera to monitor droplet generation). This setup can be further simplified using hydrostatic pressure to drive the flow. See FIG. 3C.

Figure 5:
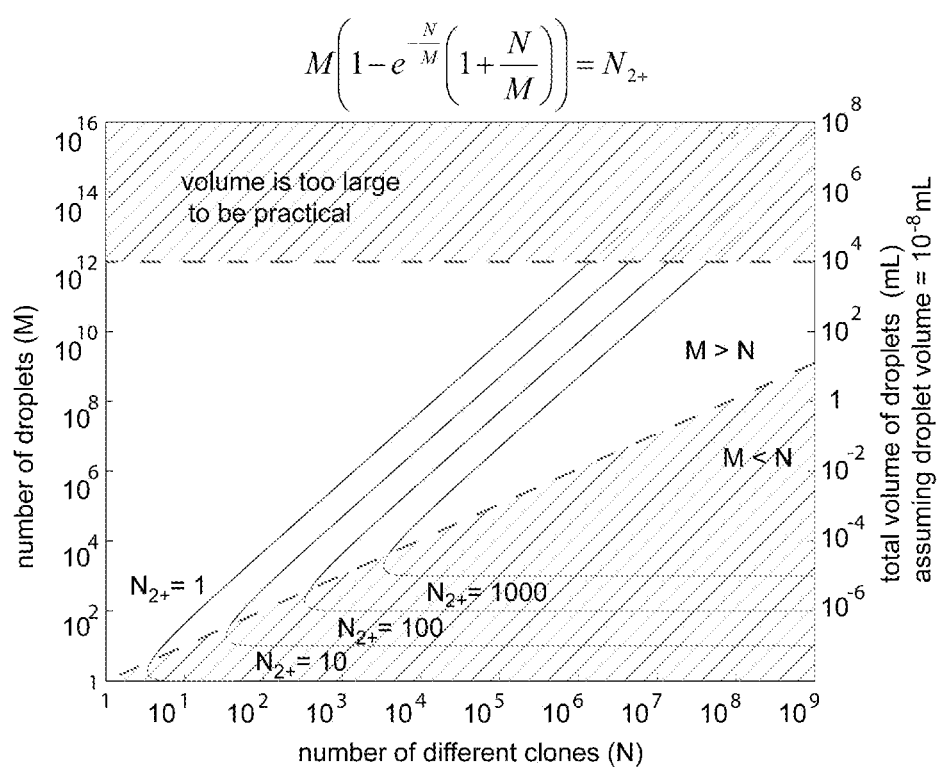
FIG. 5 shows a graph illustrating an exemplary theoretical correlation of the number of droplets or the total volume of droplets with the number of clones, in one embodiment.

FIG. 5 demonstrates (N,M) solutions for $N_{2+}$=1, 10, 100 and 1000. For example, to distribute a library that contains $10^5$ different clones in a way that minimizes the number of mixed droplets to less than one ($N_{2+}$=1), one needs M=$10^{10}$ droplets. This number requires several days of continuous droplet generation (at standard 2-3 kHz frequency for a single MFFD); more importantly, only 1 in $10^5$ droplets was infected in this example; thus, amplification using prior art techniques generates impractically dilute libraries. Large volumes of liquid have to be processed to generate a number of phage sufficient for selection (~$10^{11}$ pfu).

Amplification of large libraries (greater than $10^5$ clones) can sometimes be done at a cost of losing a certain number of clones in mixed droplets; however, doing so should not present a problem for the application of this method in a selection procedure. Although every selection starts from a library of greater than $10^9$ clones, in some cases the first round of selection usually yields less than $10^5$ clones. In this case, the vast majority of the clones do not bind the target, and hence are eliminated prior to any amplification. The remaining library of less than $10^5$ clones can be easily distributed in separate droplets and amplified.

Monodisperse emulsions therefore can be important for amplifying libraries in which every clone is of different genotype: the ratio between clones can be preserved if (1) the phage can be isolated and separated from each other, and (2) all compartments have essentially the same size. The use of limiting dilution makes clonal distribution of phage to droplets simple. Nevertheless, it is a random process and an excess of droplets is always needed to ensure that most phage clones are placed in separate droplets. With a single droplet generator operating at 2-5 kHz, the practical number of (different) phage clones that can be amplified in droplets in this example is estimated at ~$10^4$-$10^7$ (see calculations below). Phage screening starts from a library containing up to or even exceeding $10^9$ clones, and the first round of selection typically eliminates greater than 99.99% of the non-binding clones. The resulting sub-library can readily be encapsulated and amplified in droplets.

Experimental Details

Fabrication of the Microfluidic Channel.

The microfluidic channel was fabricated using standard soft lithography. A design was printed at 5000 dpi resolution on a transparency (CAD/Art Services, Inc.). This transparency served as a photomask in contact photolithography to produce a master. A 3 inch Si-wafer (Silicon Sense, Inc) was cleaned using a plasma cleaner for 5 min, and a 140 micrometer thick film of SU8-50 (Microchem) was spin-coated onto the wafer. Following instructions from Microchem, the wafer was soft-baked, exposed to UV through the photomask at 500 mJ/cm$^2$ using AB-M mask aligner, and hard-baked for 30 min. The master was then developed in SU-8 developer for 15 minutes, rinsed in isopropanol, dried, and silanized with trichloro(1H,1H,2H,2H-perfluorooctyl) silane.

To produce the top half of the microfluidic channel, PDMS elastomer base and curing agent (Dow Corning Sylgard 184) was mixed in 10:1 ratio, the sample was degassed for 30 min, and the mixture was poured onto the SU8 master. PDMS was also poured over a Petri dish to create the bottom flat half of the microfluidic channel. After incubation for greater than 1 hour in a 60° C. oven, both halves were peeled off their templating wafers, ~1×4 cm areas were cut out, and holes at the inlets of the top half of the microfluidic channel were punched using 1.2 mm biopsy puncher (Harris Uni-core). Both halves were oxidized in a plasma cleaner for 1 min and, no later than 2 minutes after oxidation, briefly pressed against one another to form a seal. The seal was strengthened by incubating the channel in an oven at 100° C. for at least 30 minutes. The channel was then coated with Aquapel glass treatment (PPG Industries) to make the channel hydrophobic.

Sealed, treated channels can be stored for at least 6 months after their fabrication with no observable change in droplet generation. An increase in R/S ratio was observed when an old channel was re-used (FIG. 6). Thus, it was hypothesized that leftover phage amplified and could potentially contaminate the microchannel, and even after autoclaving, a significant fraction of phage persisted. Fresh channel, thus, was used for every experiment.

FIG. 6 shows a plot of solutions for the equation $$M\left(1 - e^{-\frac{N}{M}}\left(1 + \frac{N}{M}\right)\right) = N_{2+}$$

which describes how many droplets (M) are required to place N phage clones such that only $N_{2+}$ of those end up in droplets with more than one phage type ("mixed droplets"). Four (M,N)-curves are presented for $N_{2+}$=1, 10, 100 and 1,000. In this example, some practical solutions reside in between the two hatched areas: the bottom hatched area designates solutions for M less than N, which are not relevant; the top hatched area designates solutions that require an impractically high number of droplets (here $10^{12}$). Solution for other values of $N_{2+}$ can be easily extrapolated visually. Amplification of large libraries (greater than $10^7$) requires large volumes and can often only be done at the cost of losing a certain fraction of the library to "mixed droplets."

Generation of and Culture in Droplets; Harvesting Phage from Droplets.

The channels were sterilized in an autoclave. The continuous phase was a perfluorocarbon (HFE7500, 3M) with 1.8% EA surfactant (RainDance Technologies, Lexington, Mass., USA), which is a PEG-PFPE amphiphilic block copolymer. Syringe pumps (Kent Scientific Corp.) were used to drive the flow of the liquids. The flow rates were 6 mL/h for the continuous phase, and 4 mL/h for the disperse phase containing bacteria and phage mixtures. Syringes were connected to the inlets of the channel using non-sterile polyethylene tubing PE60 (BD Intramedic™).

The flow of the continuous phase was started and stabilized (via FL inlet) before introduction of the bacteria and phage. After the channel was filled with perfluoro phase, 10 microliters of log culture of bacteria and 990 microliters of phage solution in lysogeny broth (LB) medium was mixed. Within 1 min, the mixture was loaded in a 1-mL syringe, and the flow was started via AQ inlet. This sequence of steps minimized the time phage and bacteria were mixed together, and minimized the possibility that the first burst of phage progeny would occur prior to the separation of all phage into droplets. If the experiment was conducted at 4° C. instead of room temperature (about 20° C.), phage production could potentially be delayed for many hours. Droplets generated in the first 20-40 sec were discarded until the flow stabilized and the drop size attained an equilibrium size. Drops were collected into a 3 cm petri dish filled with perfluorcarbon (FC40, Sigma Aldrich) to prevent coalescence of drops upon contact with the dish. The dish was then placed in a "humidity chamber" (a 14 cm-Petri dish containing a wet Kimwipe), and rocked for seven hours in the temperature-controlled shaker set to 40-60 rpm.

Once the culture was completed, the droplets floating on top of the perfluoro liquid were harvested using a P1000 pipetman and transferred to a 1.5 mL eppendorf tube. The suspension separated into a layer of droplets (top) and a layer of excess perfluoro (bottom), which was removed using a P200 pipeteman. To the remaining suspension of droplets, one-half of the volume of droplet-destabilizing solution (Raindance) was added, and the mixture was vortexed for ~10 sec and centrifuged for 2 min at 14,000 rpm. The top layer contained phage solution, the bottom layer contained the perfluorinated phase, and the bacterial pellet was positioned on the interface of the two phases. The aqueous layer was immediately used for titering (see below) or stored in a −80° C. freezer for later quantification.

Culture and Quantification of Phage and Bacteria.

A library of M13 phage engineered to express a library of 12-mer peptides and galactosidase reporter (slow phage) and F+ bacteria for amplification was purchased from New England Biosciences (Ph.D-12 kit). Wild type phage expressing neither peptide insert nor galactosidase was present at extremely low concentrations in the Ph.D-12 library; wild-type phage was isolated from this library after repetitive rounds of amplification and dilution.

Bacteria were cultured according to the manufacturer's instructions using tetracycline-containing (Tet) plates for streaking and maintenance of bacteria and antibiotic-free LB media to grow to late log-phase. To quantify the concentration of bacteria, 40 microliters of solutions containing different dilutions of bacterial solutions were spread over one-fourth of the agar plates; plates were inverted and incubated for 12-24 hours at 36° C. Plates that contained less than 50 colonies in the one-fourth plate were used for the estimate.

To quantify the concentration of phage, 180 μL of log culture of bacteria were mixed with 10 microliters of phage solution in LB medium; the mixture was added to 3 mL of warm (50° C.) 0.75% agar solution and poured onto 1.5% agar plates containing IPTG and X-gal. Plates were inverted and incubated for 12-24 hours at 36° C. For ratios 10:1 or less, both blue-(S phage) and white-colored plaques (R phage) were counted manually on the plates that contained less than 300 plaques per plate. To quantify ratios of R (white) and S (blue) plaques approaching 100:1, a dilution of phage that yielded ~5-50 blue plaques per plate and up to 10,000 white plaques per plate was selected. Blue plaques over the entire plate were counted, and white plaques were counted in a small (1×1 cm) area and extrapolated to the area of the entire plate. For R/S ratios approaching 1000:1, 12 cm-dishes were also used instead of 7 cm to provide a better estimate of white plaques.

Titering Phage in Individual Droplets.

To confirm that distribution of phage in droplets followed Poisson distribution, 400 μm droplets were generated from a solution of $2.8 \times 10^4$ pfu/mL of S phage, $1.7 \times 10^4$ pfu/mL of R phage. One mL of solution was broken into $3.0 \times 10^4$ droplets; hence, expected numbers of phage per droplet were 1 for S and 0.5 for R phage (1 R phage in every other droplet). Individual droplets were picked under a stereoscope using a P10 pipeteman and dispensed into eppendorf tubes containing 20 microliters of droplet destabilizing solution and 40 microliters of LB media. After vortexing for ~10 sec, 200 microliters of log culture of bacteria in LB were added, and the mixture was briefly vortexed, mixed with 1 mL of warm (50° C.) agar solution, and poured atop IPTG/X-Gal plates. The number of plaques resulting from titering indicated the number of phage in individual droplets (Table 1).

TABLE 1

Phage in individual droplets.

| Droplet # | | | | | | | | |
|---|---|---|---|---|---|---|---|---|
| | 1 | 2 | 3 | 4 | 5 | 6 | 7 | 8 | Predicted average |
| R phage | 1 | 0 | 3 | 1 | 2 | 0 | 2 | 2 | 0.93 pfu/droplet |
| S phage | 0 | 0 | 1 | 1 | 0 | 1 | 0 | 2 | 0.56 pfu/droplet |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention can be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of amplifying a library of replicable bacteriophage clones while maintaining diversity of the library, the method comprising:
   a. distributing a library of replicable bacteriophage clones comprising a plurality of distinguishable replicable bacteriophage clones into a plurality of monodisperse microfluidic droplets-such that substantially no more than one replicable bacteriophage clone is contained in each of the monodisperse microfluidic droplets and wherein each of the monodisperse microfluidic droplets further comprises at least one bacterial cell capable of supporting replication of the respective replicable bacteriophage clones; and
   b. culturing the library of step (a) for a sufficient period of time such that the bacterial cell in each of the monodisperse microfluidic droplets replicates to reach substantially the same number therein, and wherein the library of the replicable bacteriophage clones is amplified when the replicable bacteriophage clones present in the respective monodisperse microfluidic droplets-infect the replicated bacterial cells therein;
wherein the replicable bacteriophage clones in the library have different amplification rates, and wherein the ratio of bacteriophage clones of different amplification rates is maintained upon amplification thereby maintaining diversity of the library of replicable bacteriophage clones upon amplification.

2. The method of claim 1, wherein the number of bacterial cells within each of the monodisperse microfluidic droplets-is substantially the same.

3. The method of claim 2, wherein substantially each of the monodisperse microfluidic droplets-further comprises at least ten bacterial cells capable of supporting replication of the respective replicable viral clone.

4. The method of claim 1, wherein each of the monodisperse microfluidic droplets-further comprises growth or replication media containing substantially the same amounts of nutrients.

5. The method of claim 1, wherein each of the replicable bacteriophage clones replicates to reach a maximum copy number allowed in each of the monodisperse microfluidic droplets.

6. The method of claim 1, wherein the plurality of distinguishable replicable bacteriophage clones are distributed into a plurality of monodisperse microfluidic droplets using at least one microfluidic device.

7. The method of claim 6, wherein the monodisperse microfluidic droplets are suspended in a perfluorinated liquid and stabilized by at least one surfactant.

8. The method of claim 1, further comprising the step of releasing the amplified distinguishable replicable bacteriophage clones within monodisperse microfluidic droplets into one common fluid.

9. The method of claim 8, wherein the step of releasing is performed by adding at least one destabilization agent into the amplified library of step (b).

10. The method of claim 8, wherein the step of releasing is performed by diluting the at least one surfactant.

11. The method of claim 8, wherein the step of releasing is performed in the presence of electric fields.

12. The method of claim 1, wherein the monodisperse microfluidic droplets have an average diameter of at least about 40 μm.

13. The method of claim 1, wherein the monodisperse microfluidic droplets have an average diameter of about 20 μm to about 500 μm.

14. The method of claim 1, wherein the monodisperse microfluidic droplets have an average diameter of no larger than 200 μm.

15. The method of claim 1, wherein the library comprises at least about 100 distinguishable clones.

16. The method of claim 1, wherein the library comprises at least about 1,000 distinguishable clones.

17. The method of claim 1, wherein the library comprises at least about $10^6$ distinguishable clones.

18. The method of claim 1, wherein the library comprises at least about $10^9$ distinguishable clones.

* * * * *